United States Patent [19]
Biller et al.

[11] Patent Number: 5,312,814
[45] Date of Patent: May 17, 1994

[54] α-PHOSPHONOCARBOXYLATE SQUALENE SYNTHETASE INHIBITORS

[75] Inventors: Scott A. Biller, Ewing; David R. Magnin, Hamilton, both of N.J.

[73] Assignee: Bristol-Myers Squibb Co., Princeton, N.J.

[21] Appl. No.: 987,831

[22] Filed: Dec. 9, 1992

[51] Int. Cl.$^5$ ............... A61K 31/73; A61K 31/66; C07F 9/40; C07F 9/38
[52] U.S. Cl. ............................. 514/39; 514/54; 514/120; 558/179; 558/182; 560/102; 560/183; 560/205; 560/219; 562/24
[58] Field of Search ............ 562/24; 558/182; 560/205; 514/120, 39

[56] References Cited

U.S. PATENT DOCUMENTS 3,313,735  4/1967  McCune ............... 252/548 X
4,525,289  6/1985  Howie et al. ......... 558/170 X

OTHER PUBLICATIONS

Snider, B. B. et al. *J. Org. Chem.* 1983, 48(21), 3685–3689.
*Chem. Abstr.* 1992, 117(11), 111841; Li, Y. et al. *Chin. Chem. Lett.* 1992, 3(1), 15–18.
Marshall, J. A. et al. *J. Org. Chem.* 1986, 51(10), 1735–1741.
Eriksson, B. et al, "Pyrophosphate Analogues as Inhibitors of DNA Polymerases of Cytomegalovirus, Herpes Simplex Virus and Cellular Origin," Biochimica et Biophysica Acta, 1982, 696, 115–123.
Lofgren, B. et al, "Inhibition of RNA- and DNA-dependent duck hepatitis B virus DNA polymerase activity by nucleoside and pyrophosphate analogs," Antiviral Research, 1989, 12, 301–310.
Widell, A. et al, "Influence of twenty potentially antiviral substances on in vitro multiplication of hepatitis A virus," Antiviral Research, 1986, 6, 103–112.
Maurer, E. et al, "Long Chain α-Phosphono Fatty Acids, Salts and Esters," J. Am. Oil Chemists' Soc., 1964, 41(3), 206–208.
Ackerman, B. et al, "Phosphorus Derivatives of Fatty Acids. III.$^2$ Trialkyl α-Phosphonates" J. Am. Chem. Soc., 1957, 79, 6524–6526.
Eriksson, B. et al, "Inhibition of Herpesvirus DNA Polymerases by Foscarnet and Related Pyrophosphate Analogues" Proc. Int. Congr. Chemother. 13th, 1983, 6, 114/29–114/32.
Okamoto, Y. et al, "The properties of (α-carboxy-n-alkyl)phosphonic acids" Kogyo Kagaku Zasshi, 1966, 69(9), 1871–1875.

*Primary Examiner*—Mary C. Lee
*Assistant Examiner*—Michael Ambrose
*Attorney, Agent, or Firm*—Burton Rodney

[57] ABSTRACT

α- Phosphonocarboxylate compounds are provided which inhibit the enzyme squalene synthetase and thereby inhibit cholesterol biosynthesis. These compounds have the formula

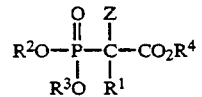

wherein
  $R^1$ is a lipophilic group which contains at least 7 carbons and is substituted alkyl, optionally substituted cycloalkyl, optionally substituted cycloalkylalkyl, optionally substituted alkenyl, optionally substituted alkynyl, optionally substituted arylalkyl or optionally substituted aryl;
  Z is H, halogen, hydroxy, hydroxyalkyl or lower alkyl;
  $R^2$ and $R^3$ are independently H, metal ion or other pharmaceutically acceptable cation, or a prodrug ester;
  $R^4$ is H, metal ion or other pharmaceutically acceptable cation, lower alkyl, lower alkenyl, arylalkyl, aryl or a prodrug ester.

17 Claims, No Drawings

α-PHOSPHONOCARBOXYLATE SQUALENE SYNTHETASE INHIBITORS

FIELD OF THE INVENTION

The present invention relates to new α-phosphonocarboxylate compounds which are useful in inhibiting cholesterol biosynthesis by inhibiting de novo squalene production, to hypocholesterolemic and antiatherosclerotic compositions containing such compounds and to a method of using such compounds for inhibiting cholesterol biosynthesis and atherosclerosis.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C.D.; Rilling, H.C., in "Biosynthesis of Isoprenoid Compounds", Vol. I, Chapter 8, pp. 413–441, J. Wiley and Sons, 1981, and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase along with HMG-CoA reductase have been shown to be down-regulated by receptor mediated LDL uptake (Faust, J.R.; Goldstein, .L.; Brown, M.S. *Proc. Nat. Acad. Sci. U.S.A.* 1979, 76, 5018–5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

U.S. Pat. No. 3,313,735 to McCune disclose shampoo compositions which include phosphono compounds of the formulae $$RN(CH_2PO_3M_2)_2 \quad or \quad (1)$$

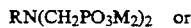
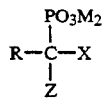
(2)

wherein R is an alkyl radical containing 6 to 18 carbons, X is H or methyl, Z is OH, COOM and $PO_3M_2$, and M is H, Na, K, ammonium, and low molecular weight substituted ammonium.

B. Eriksson et al, Biochimica et Biophysica Acta 1982, 696, 115–123 and Proc. Int. Congr. Chemother. 13th 1982, 6, 114/29–114/32 disclose inhibitors of DNA polymerases of cytomegalovirus and herpes simplex virus having the formula

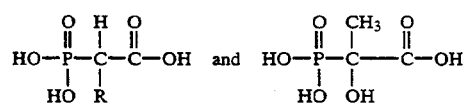

wherein R is H, $CH_3$, $CH_2CH_3$, $(CH_2)_2CH_3$, $(CH_2)_8CH_3$, phenyl or OH.

B. Lofgren et al, Antiviral Research 1989, 12, 301–310 discloses inhibitors of the DNA polymerase of hepadnaviruses having the structure

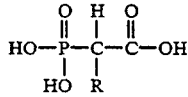

wherein R is OH, $(CH_2)_4CH_3$, $(CH_2)_6CH_3$, $(CH_2)_8CH_3$, $(CH_2)_{10}CH_3$,

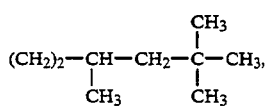

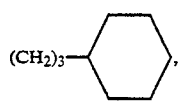

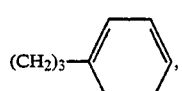

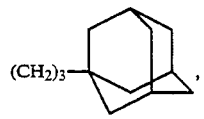

$(CH_2)_{11}-Br$, $(CH_2)_{10}-CO_2H$.

A. Widell et al, Antiviral Research 1986, 6, 103–112, discloses inhibitors of hepatitis A virus having the structure

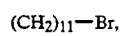
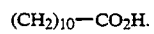

E.W. Maurer et al, J. Am. Oil Chemists' Soc., 1964, 41(3), 206–208, discloses α-phosphono fatty acids, esters and their salts having the structure

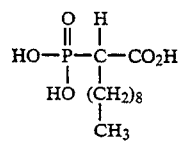

wherein R is $(CH_2)_6CH_3$ to $(CH_2)_{15}CH_3$ and $R^a$ is H or methyl, isopropyl or aryl esters (containing 14 to 19 carbons in total).

B. Ackerman et al, J. Am. Chem. Soc. 1957, 79, 6524–6526 discloses triethyl esters of α-phosphono acid of the structure

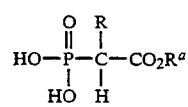

wherein R is $C_2H_5$ to $C_{16}H_{33}$.

Y. Okamoto et al, Kogyo Kagaku Zasshi 1966, 69(9), 1871–1875, disclose surface-active agents and detergents having the formula

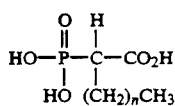

wherein n is 9, 11, 13 or 15.

DESCRIPTION OF THE INVENTION

In accordance with the present invention, there is provided α-phosphonocarboxylate compounds which inhibit cholesterol biosynthesis, and thus are useful as hypocholesterolemic and antiatherosclerotic agents and have the following structure I

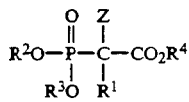

wherein $R^2$ and $R^3$ are the same or different and are H, a metal ion, or other pharmaceutically acceptable cations, or a prodrug ester;

$R^4$ is H, lower alkyl, lower alkenyl, aryl, arylalkyl, metal ion, or other pharmaceutically acceptable cations, or a prodrug ester;

Z is H, halogen, lower alkyl, hydroxy or hydroxyalkyl;

$R^1$ is a lipophilic group containing at least 7 carbons and is substituted alkyl, optionally substituted cycloalkyl, optionally substituted cycloalkylalkyl, optionally substituted alkenyl, optionally substituted alkynyl, optionally substituted arylalkyl or optionally substituted aryl. The above $R^1$ groups may be substituted with 1 to 4 groups which may be alkyl, alkenyl, alkynyl, halogen, hydroxy, alkoxy, alkenyloxy, alkynyloxy, aryl, cycloalkyl, arylalkyl, amino, alkylamido, alkanoylamino, arylcarbonylamino, nitro, cyano, thiol and/or alkylthio.

The term "prodrug esters" as employed herein includes, but is not limited to, the following groups: (1-alkanoyloxy)alkyl such as,

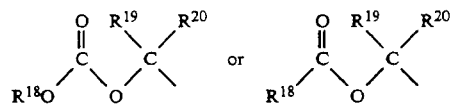

wherein $R^{18}$ is alkyl, aryl or arylalkyl, and $R^{19}$ and $R^{20}$ are H, alkyl, aryl or aryl-alkyl. Examples of such prodrug esters include $CH_3CO_2CH_2—$,

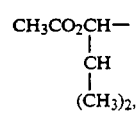

$t\text{-}C_4H_9CO_2CH_2—$, or

-continued

Other examples of suitable prodrug esters include

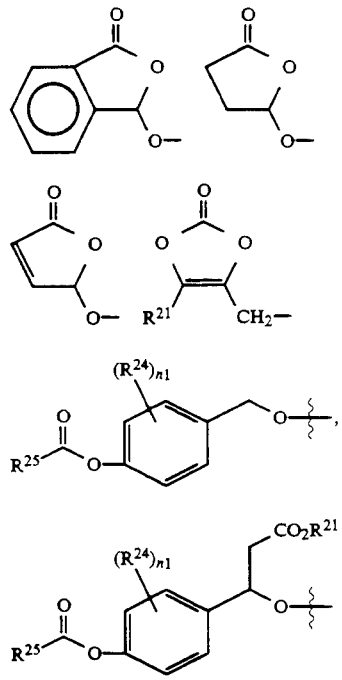

wherein $R^{21}$ can be H, alkyl (such as methyl or t-butyl), or aryl (such as phenyl); $R^{24}$ is H, alkyl, halogen or alkoxy, $R^{25}$ is alkyl, aryl, arylalkyl or alkoxyl, and $n_1$ is 0, 1 or 2; or $R^2$ and $R^3$ can be taken together as in

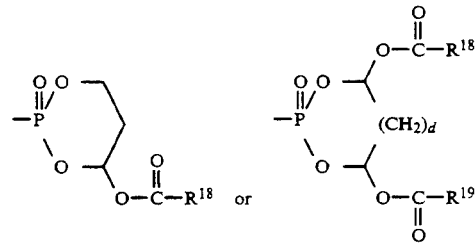

(d is 0 to 3)

Unless otherwise indicated, the term "lower alkyl" or "alkyl" as employed herein alone or as part of another group includes both straight and branched chain hydrocarbons, containing 1 to 40 carbons, preferably 1 to 25 carbons, in the normal chain, more preferably 1 to 10 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as F, Br, Cl or I or CF_3, alkoxy, aryl, arylalkyl, alkenyl, alkenyloxy, cycloalkyl, amino, hydroxy, alkylamido, alkanoylamino, arylcarbonylamino, nitro, cyano, thiol and/or alkylthio.

The term "lower alkyl" is as defined for "alkyl" except that it will contain 1 to 12 carbons, preferably 1 to 8 carbons.

Unless otherwise indicated, the term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 to 4 substituents such as halogen, alkyl, alkoxy, hydroxy, aryl, arylalkyl, cycloalkyl, alkylamido, alkanoylamino, arylcarbonylamino, amino, nitro, cyano, thiol and/or alkylthio.

Unless otherwise indicated, the term "aryl" or "Ar" as employed herein refers to monocyclic or bicyclic aromatic groups containing from 6 to 10 carbons in the ring portion, such as phenyl, naphthyl or phenyl or naphthyl substituted with 1 to 3 substituents such as alkyl, halogen (Cl, Br or F), alkoxy, hydroxy, amino, alkanoylamino, arylcarbonylamino, aryl, arylalkyl, cycloalkyl, alkylamido, nitro, cyano, thiol and/or alkylthio.

The term "aralkyl", "aryl-alkyl" or "aryl-lower alkyl" as used herein alone or as part of another group refers to alkyl groups as discussed above having an aryl substituent, such as benzyl or phenethyl.

The term "lower alkoxy", "alkoxy", "aryloxy" or "aralkoxy" as employed herein alone or as part of another group includes any of the above alkyl, aralkyl or aryl groups linked to an oxygen atom.

The term "lower alkylthio", alkylthio", "arylthio" or "aralkylthio" as employed herein alone or as part of another group includes any of the above alkyl, alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 40 carbons, preferably 2 to 30 carbons in the normal chain, which include one to three double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like, and which may be optionally substituted with 1 to 4 substituents, namely, halogen, alkyl, alkoxy, alkenyl, alkynyl, aryl, arylalkyl, cyclo-alkyl, amino, hydroxy, alkanoylamino, alkylamido, arylcarbonylamino, nitro, cyano, thiol and/or alkylthio.

Unless otherwise indicated, the term "lower alkynyl" or "alkynyl" as used herein by itself or as part of another group refers to straight or branched chain radicals of 2 to 40 carbons, preferably 2 to 20 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4 -heptynyl, 3-octynyl, 3-nonynyl, 4-decynyl,1,3-undecynyl, 4-dodecynyl and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkyl-amido, arylcarbonylamino, nitro, cyano, thiol, and/or alkylthio.

The term "halogen" or "halo" as used herein refers to chlorine, bromine, fluorine, and iodine as well as $CF_3$, with chlorine or fluorine being preferred.

The term "amino" as used herein refers to unsubstituted amino as well as monouubstituted amino or disubstituted amino wherein the substituents may be alkyl and/or aryl.

The term "metal ion or other pharmaceutically acceptable cations" as employed herein refers to lithium, sodium or potassium, alkaline earth metal salts such as calcium or magnesium, as well as zinc or aluminum and other FDA approved cations such as ammonium, choline, diethanolamine, ethylenediamine, and salts of naturally occuring amino acids such as arginine, lysine, alanine and the like.

The term "haloalkyl" as used herein refers to any of the lower alkyl groups defined above substituted with a halogen as defined above, for example $CH_2F$, $CF_3$ and the like.

Preferred are those compounds of formula I wherein Z is H, halo such as fluoro or chloro, hydroxy or hydroxymethyl, $R^1$ is alkenyl containing 2 or 3 double bonds such as

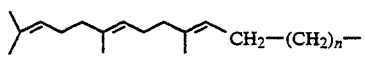

(wherein n is 1, 2 or 3)

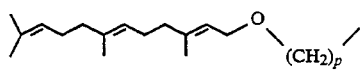

(wherein p is 1 or 2),

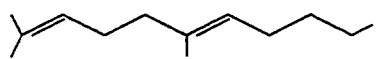

or biphenylalkylene such as

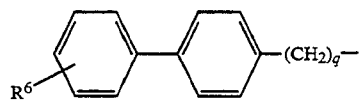

(wherein q is 3 to 6) wherein
$R^6$ is H or lower alkyl;
$R^2$, $R^3$ are Na, K or H, and
$R^4$ is H, Na or K.

The formula I compounds of the invention include all stereoisomers thereof.

The compounds of the invention may be prepared as follows.

Compounds of formula I may be prepared starting with the phosphonocarboxylate II

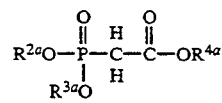

II wherein $R^{2a}$, $R^{3a}$ and $R^{4a}$ are independently lower alkyl, which is made to undergo a coupling reaction wherein II is treated with a base such as sodium hydride, potassium hydride or potassium tert-butoxide, and a halide III

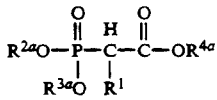

wherein Hal is I or Cl, in the presence of an inert organic solvent such as dimethylformamide (DMF), tetrahydrofuran (THF) or diethyl ether, to form the coupled product triester IA of the invention

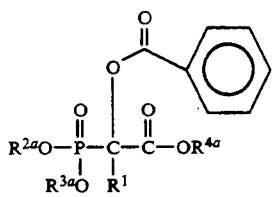

The above coupling reaction is carried out at a temperature within the range of from about −78° to about 100° C., preferably from about 0° to about 40° C. employing a molar ratio of III to II of within the range of from about 10:1 to about 0.1:1 and preferably from about 1:1 to about 0.3:1.

Compounds of the invention wherein X is halogen, hydroxy, hydroxymethyl or lower alkyl may be prepared from triester IA as follows.

Where X is a halogen, triester IA is treated with a base which is sodium bis(trimethylsilyl)amide, sodium hydride or lithium bis(trimethylsilyl)amide in the presence of an inert organic solvent such as tetrahydrofuran (THF), diethyl ether or dimethylformamide and then with an electrophile namely, N-chlorosuccinimide (NCS), N-fluorobenzenesulfonimide or N-bromosuccinimide (NBS), to form the α-phosphonocarboxylate IB

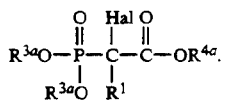

The above reaction is carried out at a temperature within the range of from about −78° to about 60° C., preferably from about −78° to about 0° C., employing a molar ratio of electrophile (such as N-chlorosuccinimide) to IA of within the range of from about 10:1 to about 0.7:1, preferably from about 2:1 to about 0.8:1.

Compounds of the invention wherein X is lower alkyl such as methyl may be prepared by treating triester IA with a base which is sodium bis(trimethylsilyl)amide, sodium hydride or potassium bis(trimethylsilyl)amide, in the presence of an inert organic solvent such as tetrahydrofuran (THF), dimethylformamide (DMF) or diethyl ether and then with an alkyl halide such as methyl iodide, ethyl iodide, propyl iodide or ethyl bromide, to form the α-phosphoncarboxylate IC

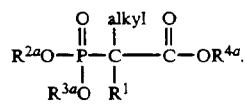

The above reaction is carried out at a temperature within the range of from about −78° to about 100° C., preferably from about −78° to about 0° C., employing a molar ratio of alkyl halide to IA of within the range of from about 10:1 to about 0.6:1, preferably from about 3:1 to about 0.8:1.

Compounds of the invention of formula I where X is hydroxy may be prepared by treating triester IA with a base such as sodium bis(trimethylsilyl)amide, sodium hydride or potassium bis(trimethylsilyl)amide, in the presence of an inert organic solvent such as tetrahydrofuran (THF), dimethylformamide (DMF) or diethyl ether and then with an oxidizing agent such as dibenzoyl peroxide, to form the α-phosphonocarboxylate ID

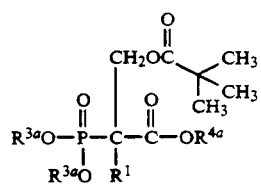

The above reaction is carried out at a temperature within the range of from about −78° to about 30° C., preferably from about −78° to about 0° C., employing a molar ratio of oxidizing agent to IA of within the range of from about 10:1 to about 0.7:1, preferably from about 3:1 to about 0.8:1.

Compounds of the invention wherein X is hydroxymethyl may be prepared by treating triester IA with a base such as sodium hydride, sodium bis(trimethylsilyl)amide or potassium bis(trimethylsilyl)amide, in the presence of an inert organic solvent such as tetrahydrofuran (THF), diethyl ether or dimethylformamide (DMF) and then with an electrophile such as iodomethyl pivalate, to form the α-phosphonocarboxylate IE $$\begin{array}{c} O \\ \| \\ CH_2OC \end{array}\begin{array}{c} CH_3 \\ CH_3 \\ CH_3 \end{array}$$

(placeholder — see image)

The above reaction is carried out at a temperature within the range of from about −78° to about 100° C., preferably from about −78° to about 0° C., employing a molar ratio of electrophile (such as iodomethyl pivalate) to IA of within the range of from about 10:1 to about 0.1:1, preferably from about 3:1 to about 0.8:1.

In an alternative method for preparing compounds of the invention (I) where Z is halogen, or lower alkyl, the Z group can be added to the triester starting material II, before R¹, as follows.

Where Z is F, Cl or lower alkyl, trialkyl phosphite V

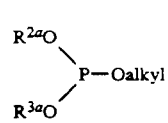

is treated with an ester of the structure VI

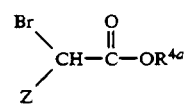

(Z is Cl, F or lower alkyl)

at a temperature within the range of from about 0 to about 200° C. and preferably from about 50° for about 150° C. to form the starting material IIA $$R^{2a}O-\overset{O}{\underset{R^{3a}O}{\overset{\|}{P}}}-\overset{Z}{\underset{H}{C}}-\overset{O}{\overset{\|}{C}}-OR^{4a} \quad \text{IIA}$$

The starting material IIA may then be treated with base such as sodium hydride, sodium bis(trimethylsilyl)amide or potassium bis(trimethylsilyl)amide and halide III $$R^1Hal \quad \text{III}$$

in the presence of an inert organic solvent such as THF to form the phosphonocarboxylate IB.

The above reaction is carried out at a temperature within the range of from about −78° to about 100° C., preferably from about 0° to about 50° C., employing a molar ratio of III to IIA of within the range of from about 10:1 to about 0.7:1, preferably from about 1:1 to about 0.8:1.

Where Z is lower alkyl, phosphonocarboxylate II is treated with a lower alkyl halide IIIA $$ZHal \quad \text{IIIA}$$

and a base, such as sodium hydride, sodium bis(trimethylsilyl)amide or potassium bis(trimethylsilyl)amide, in the presence of an inert organic solvent such as DMF, tetrahydrofuran (THF) or diethyl ether. This reaction is carried out at a temperature within the range of from about −78° to about 100° C., preferably from about −20° to about 20° C., employing a molar ratio of IIIA:II of within the range of from about 10:1 to about 0.7:1, preferably from about 2:1 to about 0.8:1.

In another alternative method for preparing compounds of the invention I wherein $R^1$ is $R^{1a}OCH_2$ and $R^{1a}$ is alkyl, alkenyl, alkynyl, aryl or arylalkyl, triester VII $$R^{2b}O-\overset{O}{\underset{R^{3b}O}{\overset{\|}{P}}}-\overset{CH_2}{\overset{\|}{C}}-\overset{O}{\overset{\|}{C}}OR^{4b} \quad \text{VII}$$

wherein $R^{2b}$, $R^{3b}$ and $R^{4b}$ are allyl or substituted allyl, preferably —CH$_2$—CH=CH$_2$, is treated with alcohol VIII $$R^{1a}OH \quad \text{VIII}$$

under an inert atmosphere such as argon, employing a molar ratio of VIII:VII of within the range of from about 20:1 to about 0.5:1, preferably from about 4:1 to about 0.8:1, to form the coupled reaction product IG.

$$R^{2b}O-\overset{O}{\underset{R^{3b}O}{\overset{\|}{P}}}-\overset{H}{\underset{CH_2OR^{1a}}{\overset{|}{C}}}-\overset{O}{\overset{\|}{C}}-OR^{4b} \quad \text{IG}$$

The phosphoncarboxylate IG may be treated under an inert atmosphere such as argon, with dimethylethyl silane, diphenylsilane or triethylsilane; tetrakis(triphenylphosphine)palladium; and triphenyl phosphine followed by base such as alkali metal hydroxide and methanol, to form the corresponding metal salt IH $$MO-\overset{O}{\underset{MO}{\overset{\|}{P}}}-\overset{H}{\underset{CH_2OR^{1a}}{\overset{|}{C}}}-\overset{O}{\overset{\|}{C}}-OM \quad \text{IH}$$

The above reaction may be carried out employing molar ratios as follows:

silane compound: IG = 100:1 to 3:1
palladium compound: IG = 1:1 to 0.01:1
triphenylphosphine: IG = 10:1 to 0.02:1
alkali metal hydroxide: IG = 20:1 to 3:1.

The triester compounds IA of the invention IA, IB, IC, ID, IE may be converted to various salts employing the following deprotecting reactions.

Deprotecting Reactions:

(1)
$$R^{2a}O-\overset{O}{\underset{R^{3a}O}{\overset{\|}{P}}}-\overset{Z}{\underset{R^1}{\overset{|}{C}}}-\overset{O}{\overset{\|}{C}}OR^{4a} \xrightarrow[\text{Hydrolysis}]{\text{Base}} R^{2a}O-\overset{O}{\underset{R^{3a}O}{\overset{\|}{P}}}-\overset{Z}{\underset{R^1}{\overset{|}{C}}}-\overset{O}{\overset{\|}{C}}OH$$

IA, IB, IC, IE        IJ $$\text{IJ} \xrightarrow[\text{2) H}_2\text{O or CH}_3\text{OH}]{\text{1) Bromotrimethylsilane (TMSBr)}} HO-\overset{O}{\underset{HO}{\overset{\|}{P}}}-\overset{Z}{\underset{R^1}{\overset{|}{C}}}-\overset{O}{\overset{\|}{C}}OH \xrightarrow{\text{Base}}$$

IK $$^{\ominus}O-\overset{O}{\underset{^{\ominus}O}{\overset{\|}{P}}}-\overset{Z}{\underset{R^1}{\overset{|}{C}}}-\overset{O}{\overset{\|}{C}}CO^{\ominus}$$

IL (2)
$$\text{IA, IB, IC, ID, IE} \xrightarrow{\text{Iodotrimethylsilane (TMSI)}}$$

$$\text{IK} \xrightarrow[\text{Optional heat}]{\text{Base}} \text{IL}$$

(3)
$$\text{IA, IB, IC, ID, IE} \xrightarrow[\text{2) H}_2\text{O or CH}_3\text{OH}]{\text{1) Bromotrimethylsilane (TMSBr)}}$$

$$HO-\overset{O}{\underset{HO}{\overset{\|}{P}}}-\overset{Z}{\underset{R^1}{\overset{|}{C}}}-\overset{O}{\overset{\|}{C}}OR^{4a} \xrightarrow{\text{Base}} \text{IN}$$

IM $$^{\ominus}O-\overset{O}{\underset{^{\ominus}O}{\overset{\|}{P}}}-\overset{X}{\underset{R^1}{\overset{|}{C}}}-\overset{O}{\overset{\|}{C}}COR^{4a} \xrightarrow[\text{Heat}]{\text{Base}} \text{IL}$$

IN

In the case of ID and IE, the benzoate and pivolate protecting groups, respectively, are removed upon heating with base in the final step (that is, IK and IN to IL) employing Methods (2) or (3) as set out above.

In the above deprotecting reactions, in Method (1), the triester is treated with a strong aqueous base such as NaOH, KOH or LiOH, typically in the presence of a solvent such as dioxane, isopropanol, methanol or ethanol at a temperature within the range of from about 25° to about 125° C. to form diester of the invention IJ.

Diester IJ is subjected to a bisdealkylation by treating IJ with bromotrimethylsilane under an inert atmosphere such as argon in the presence of 2,4,6-collidine or hexamethyldisilizane in dichloromethane followed by treatment with water or methanol to form acid IK which is treated with base (as described above in forming IJ) to form IL.

In Method (2) the triester is treated with iodotrimethylsilane under an inert atmosphere such as argon in the presence of 2,4,6-collidine or hexamethyldisilizane to form acid IK directly which is treated with base (as described above in forming IJ) to form IL.

In Method (3) the triester is treated with bromotrimethylsilane (as described in Method (1)) to form monoester IM which is treated with base (as described hereinbefore) to form the salt IN which is treated with base at elevated temperature (60°–120° C.) to form IL.

In addition, the deprotections illustrated for the conversion of IG to IH as set out above may be generally applicable as follows:

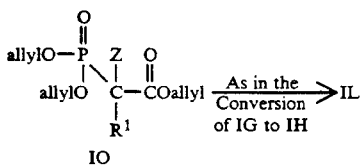

Examples of starting $R^1Hal$ III or $R^{1a}OH$ VIII (starting material) suitable for use herein include the following which are either known in the literature or are simple derivatives of known compounds prepared by employing conventional procedures.

It will be appreciated that the compounds III and VIII listed in the following table represent all possible stereoisomers.

| $R^1$ of $R^1Hal$ or $R^{1a}$ of $R^{1a}OH$ | | |
|---|---|---|
| A. $R^{17}$ \\C=CH\\ /CH_2\\ /C=CH\\ /CH_2\\ /C=CH\\ (CH_2)_{n'}$ with $R^{18}$, $CH_3$, $CH_3$ | | |
| $R^{17}$ \\C=CH\\ /CH_2\\ /C=CH\\ (CH_2)_n$ or $R^{17}$ \\C=CH\\ (CH_2)_{\overline{n}}$ with $R^{18}$, $CH_3$, $R^{18}$ | | |
| n is 1 to 8 | | |
| | $R^{17}$ | $R^{18}$ |
| 1. | $C_2H_5$ | $CH_3$ |
| 2. | $CH_3$ | $C_2H_5$ |
| 3. | $n\text{-}C_3H_7$ | $CH_3$ |
| 4. | $CH_3$ | $n\text{-}C_4H_9$ |
| 5. | $t\text{-}C_4H_9$ | $CH_3$ |
| | $-(CH_2)_{s'}-$ | |
| | $s' = 4$ to 6 | |
| 7. | H | H |
| 8. | F | F |
| 9. | Cl | Cl |
| 10. | $CH_2F$ | $CH_3$ |
| 11. | $-CH=CH_2$ | H |
| 12. | $CF_3(CH_2)_t$ | H |
| | t = 0 to 8 | |

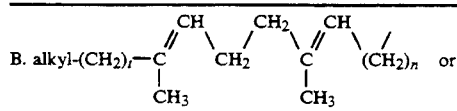

-continued

| $R^1$ of $R^1Hal$ or $R^{1a}$ of $R^{1a}OH$ |
|---|
| alkyl-$(CH_2)_t$—$\underset{CH_3}{\underset{|}{C}}$ $\overset{CH_2}{\diagup}$ $\overset{CH}{\diagdown}$ $(CH_2)_n$ (n is 1 to 8) | alkyl$(CH_2)_t$—

1. $CH_3(CH_2)_t$ where t is 0 to 8

2. $\underset{CH_3}{\underset{|}{\overset{CH_3}{\overset{|}{C}}}}-(CH_2)_t$— where t is 0 to 8
   $\quad\quad H$ 3. R—⌬—$(CH_2)_t$— where t is 0 to 8

4. R—⌬—$(CH_2)_t$— where t is 0 to 8

5. $R_1$—[naphthyl]—$R_2$, $(CH_2)_t$

6. $R_1$—[naphthyl]—$R_2$, $(CH_2)_t$—

7. $CF_3(CH_2)_t$—

8. $\underset{CF_3}{\underset{/}{\overset{CF_3}{\overset{\diagdown}{CH}}}}$—$(CH_2)_t$—

9. $R_3$—⌬—O—$(CH_2)_t$—

10. ⌬—$\underset{R}{\overset{H}{N}}$—$(CH_2)_t$—

11. $R_3$—⌬—S—$(CH_2)_t$

12. $(CH_2)_x$—[ring]—$(CH_2)_t$—

Examples 5 to 12, t=0 to 8
$R^1$, $R^2$, $R^3$=H, alkyl, alkenyl, aryl, halogen, alkoxy

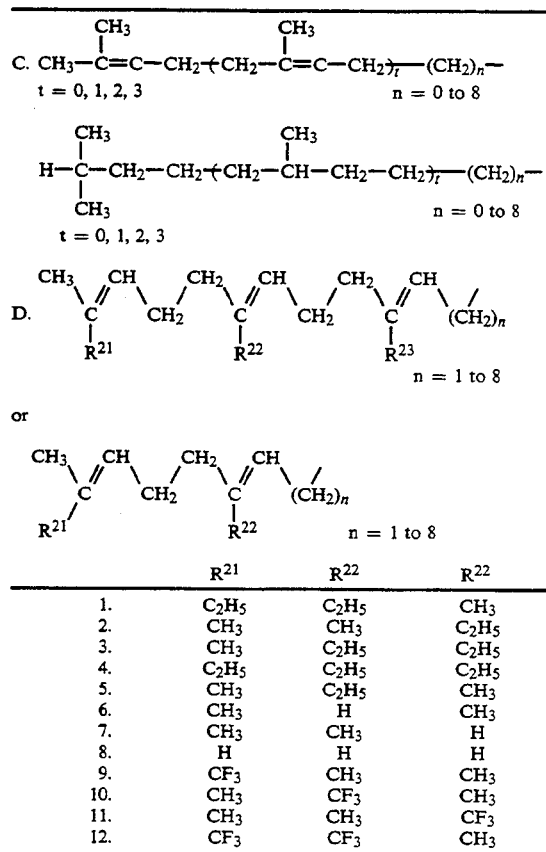
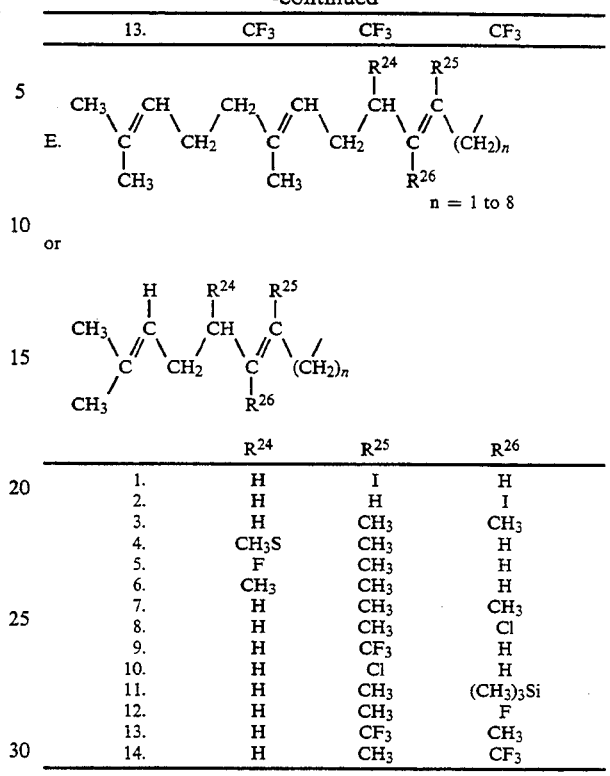
| | $R^{24}$ | $R^{25}$ | $R^{26}$ |
|---|---|---|---|
| 1. | H | I | H |
| 2. | H | H | I |
| 3. | H | $CH_3$ | $CH_3$ |
| 4. | $CH_3S$ | $CH_3$ | H |
| 5. | F | $CH_3$ | H |
| 6. | $CH_3$ | $CH_3$ | H |
| 7. | H | $CH_3$ | $CH_3$ |
| 8. | H | $CH_3$ | Cl |
| 9. | H | $CF_3$ | H |
| 10. | H | Cl | H |
| 11. | H | $CH_3$ | $(CH_3)_3Si$ |
| 12. | H | $CH_3$ | F |
| 13. | H | $CF_3$ | $CH_3$ |
| 14. | H | $CH_3$ | $CF_3$ |
F. Other examples of $R^1$ and $R^{1a}$ include the following
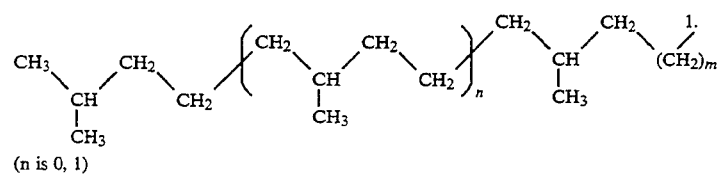
(n is 0, 1)
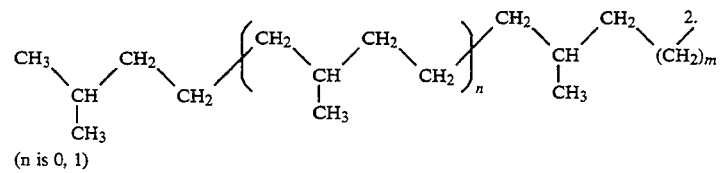
(n is 0, 1)
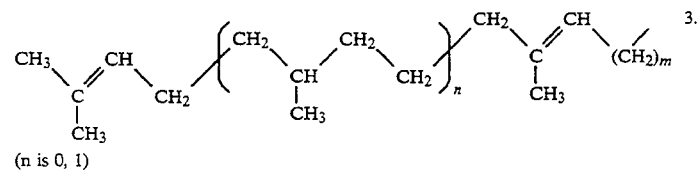
(n is 0, 1)
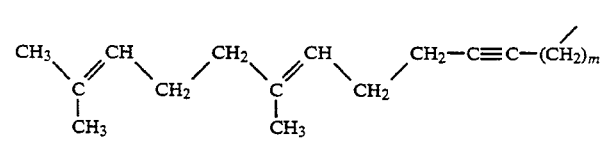
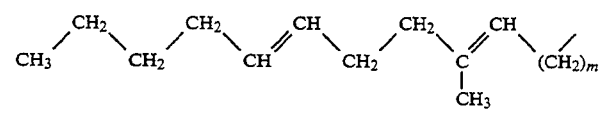

6.

(n is 1, 2)

(n is 0, 1, 2)

In Examples 1 to 5, m is 1 to 8.
In Examples 6 and 7, m is 0 to 8.

-continued

8.

9.

10.

11.

(m is 0, 1, 2)

12.

13.

In Examples 8 to 13, n is 1 to 8.

14.

(n is 1 to 8)

15.

(n is 1 to 8)

-continued

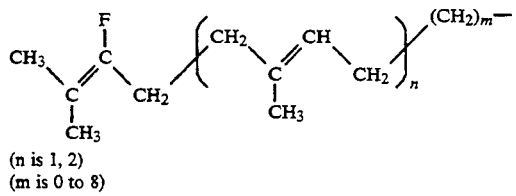
16.
(n is 1, 2)
(m is 0 to 8)

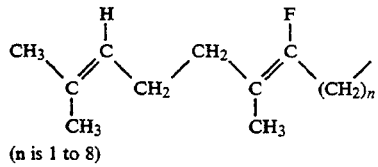
17.
(n is 1 to 8)

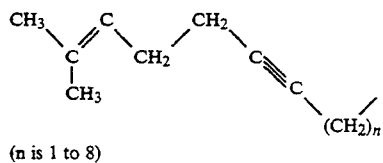
18.
(n is 1 to 8)

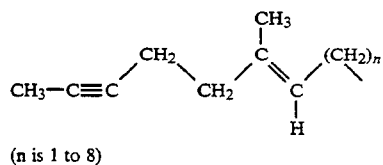
19.
(n is 1 to 8)

$CH_3-C\equiv C-(CH_2)_n-$  20.
(n = 4-12)

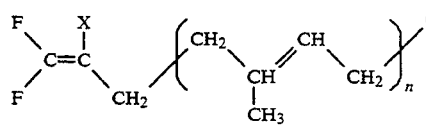
21.
X = H, F, CH$_3$
n is 1 or 2
m is 0 to 8

$CH_3-C\equiv C-(CH_2)_n-C\equiv C-(CH_2)_m-$  22.
(n = 2-10)
(m is 0 to 8)

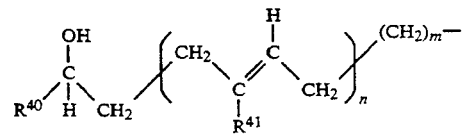
23.
n is 1 or 2
m is 0 to 8

$R^{40}$=H, alkyl, cycloalkyl, or aryl such as methyl, ethyl, isopropyl, pentyl, phenyl and cyclopentyl
$R^{41}$=alkyl such as methyl, ethyl or halo such as Cl or F

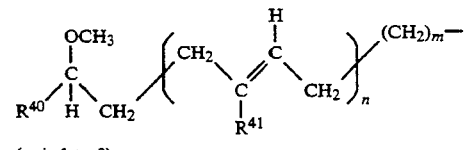
24.
(m is 1 to 8)
(n is 1 to 3)

-continued

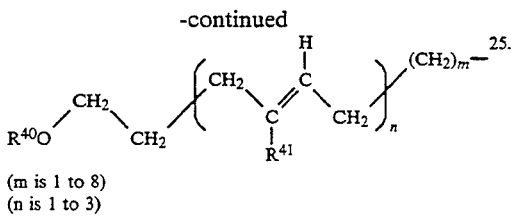
25.
(m is 1 to 8)
(n is 1 to 3)

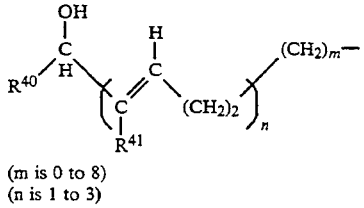
26.
(m is 0 to 8)
(n is 1 to 3)

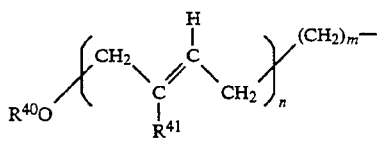
27.
(m is 0 to 8)
(n is 1 to 3)

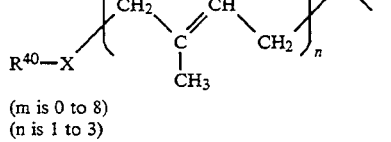
28.
(m is 0 to 8)
(n is 1 to 3)
(X is O, S, NH)

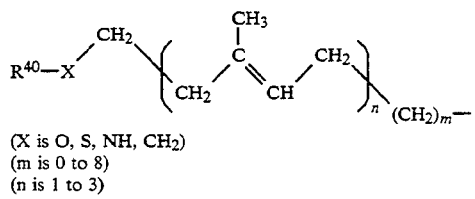
29.
(X is O, S, NH, CH$_2$)
(m is 0 to 8)
(n is 1 to 3)

Additional examples of $R^1$ or $R^{1a}$ within the scope of the present invention are set out below.

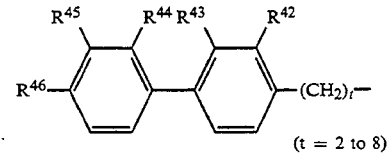
(t = 2 to 8)

| | $R^{42}$ | $R^{43}$ | $R^{44}$ | $R^{45}$ | $R^{46}$ |
|---|---|---|---|---|---|
| 30) | H | H | H | H | n-C$_3$H$_7$ |
| 31) | H | H | H | H | n-C$_4$H$_9$ |
| 32) | H | H | H | H | (CH$_3$)$_2$-C=CH- |
| 33) | H | H | H | H | (CH$_3$)$_2$-C=CH-CH$_2$- |
| 34) | CH$_3$ | H | CH$_3$ | H | ▷-CH$_2$- |
| 35) | H | H | CH$_3$ | H | (CH$_3$)$_2$-CH-CH$_2$-O- |
| 36) | H | CH$_3$ | CH$_3$ | H | n-C$_3$H$_7$ |
| 37) | CH$_3$O | H | H | H | n-C$_4$H$_9$ |
| 38) | H | H | H | H | (CH$_3$)$_2$-C=CH- |
| 39) | H | H | H | H | (CH$_3$)$_2$-C=CH-CH$_2$- |

-continued

[Structure: biphenyl with R45, R44, R43, R42 substituents on rings and R46, with -(CH2)t- chain, t = 2 to 8]

| | $R^{42}$ | $R^{43}$ | $R^{44}$ | $R^{45}$ | $R^{46}$ |
|---|---|---|---|---|---|
| 40) | $CH_3$ | H | H | H | cyclopropyl-$CH_2-$ |
| 41) | F | H | $CH_3$ | H | $n\text{-}C_3H_7$ |
| 42) | $CH_3$ | H | F | H | $n\text{-}C_4H_9$ |
| 43) | H | $CH_3$ | H | $CH_3$ | $(CH_3)_2\text{-}C\text{=}CH-$ |
| 44) | H | H | H | $CF_3$ | $(CH_3)_2\text{-}C\text{=}CH\text{-}CH_2-$ |
| 45) | H | H | H | F | cyclopropyl-$CH_2-$ |
| 46) | H | Cl | Cl | H | $CH_2\text{=}CH\text{-}CH_2-$ |
| 47) | $CH_3$ | H | H | H | $C_4H_9$ |
| 48) | H | H | OH | H | $C_3H_7$ |
| 49) | H | H | $OCH_3$ | H | $C_3H_7$ |
| 50) | H | H | $CH_3$ | H | $C_3H_7$ |
| 51) | H | OH | H | H | $C_3H_7$ |
| 52) | H | $OCH_3$ | H | H | $C_3H_7$ |
| 53) | H | $CH_3$ | H | H | $C_3H_7$ |

54) [Structure: 2,6-dimethylbiphenyl with R on one ring and $X^1-$ on the other]

55) [Structure: biphenyl with 2',6'-dimethyl substitution, R and $X^1-$]

$X^1 = -(CH_2)_n-, -CH\text{=}CH\text{-}CH_2-$
n = 2 to 8

56) [Structure: biphenyl R-...-$(CH_2)_m-$]
m = 2 to 8

Re 54) to 56)
R is $n\text{-}C_3H_7$, $n\text{-}C_4H_9$, $(CH_3)_2\text{-}C\text{=}CH-$, $CH_3\text{-}CH\text{=}CH\text{-}CH_2-$, $CH_2\text{=}CH\text{-}CH_2O-$, $(CH_3)_2\text{-}CH\text{-}O-$, cyclopropyl-$CH_2-$, $CH_2\text{=}CH\text{-}CH_2-$ 57) [Structure: polyprenyl-type chain with phosphonate group]

$R^2$ and $R^3$ are independently H, metal ion, or other pharmaceutically acceptable salt, or prodrug ester;
$R^4$ is H, metal ion, other salts, alkyl, aralkyl, aryl or prodrug ester.
Z = Cl, F, alkyl such as methyl, ethyl or propyl, OH, $CH_2OH$
n = 0, 1, 2
$p^1$ = 0-8

[Structure: diaryl ether with phosphonate]

Z is Cl, F, alkyl such as methyl, ethyl or propyl, OH, $CH_2OH$;
X is O, S, NH, SO, $SO_2$, $CHOR^5$, bond;
$R^1$, $R^2$, $R^3$, $R^4$, $R^5$ are independently H, halogen, $C_1\text{-}C_5$alkyl, $C_1\text{-}C_5$alkenyl, $C_1\text{-}C_5$alkoxy;
M = metal ion, H, pharmaceutically acceptable salt or prodrug ester.

[Structure: naphthyl-X-phenyl with $(CH_2)_p$-C(CO_2M)(PO_3M_2)]

[Structure: naphthyl-X-phenyl with $(CH_2)_p$-C(CO_2M)(PO_3M_2)]

[Structure: dibenzo ring with X and $(CH_2)_n$ bridges, with $(CH_2)_p$-C(CO_2M)(PO_3M_2)]

X = bond, O, NH, S, $CH_2$
p = 1 to 8
n = 0 to 3

M=metal ion, H, pharmaceutically acceptable salt or prodrug ester.

The compounds of Formula I of the invention inhibit cholesterol biosynthesis by inhibition of de novo squalene production. These compounds inhibit the squalene synthetase enzyme and, in addition, some of the compounds of Formula I of the invention inhibit other enzymes in the pathway from isopentenyl diphosphate to squalene, that is, farnesyl diphosphate synthetase and isopentenyl diphosphatedimethylallyl diphosphate isomerase.

Thus, the compounds of the invention are useful in treating atherosclerosis to inhibit progression of disease and in treating hyperlipidemia to inhibit development of atherosclerosis. In addition, the compounds of the invention may increase plasma high density lipoprotein cholesterol levels.

The compounds of the invention may also be useful in inhibiting formation of gallstones, treating tumors, lowering blood pressure, lowering blood sugar, treating diabetes mellitus, treating inflammation, as a diuretic, as an inotropic agent, as an antiarthritic (antirheumatic) agent, in treating other diseases of calcium and phosphate metabolism including treatment of bone resorption, Paget's disease, osteoporosis, calcification of joints, implants and metastasis, as antitartar and anticalculus agents in toothpastes and mouthwashes, treating various stones and calculi, treating sickle cell anemia, treating hypoxia and ischemic tissue, treating hepatitis D, as an anti-fungal agent, and as an anti-ameobal agent, as well as for use in complexes with technetium-99m and radioiodinated derivatives for use as diagnostics.

U.S. application Ser. No. 774,957, filed Oct. 11, 1991, discloses that post-translational modification of CAAX box containing proteins may be inhibited by administering a protein-prenyl transferase inhibitor which inhibits the transfer of the prenyl group [such as farnesyl (in the case of ras oncogene products), geranyl or geranylgeranyl] to the cysteine of the CAAX box by the protein-prenyl transferase enzyme. The protein-prenyl transferase inhibitor will block the protein-prenyl transferase enzyme from catalyzing the transfer of the prenyl group (for example, farnesyl, geranyl or geranyl-geranyl) from the prenyl pyrophosphate to the cys residue of the CAAX box, such as the ras p21 cys, or to the CAAX box cysteine of other CAAX box containing proteins. In the case of ras p21 oncogene products, inasmuch as the cys is not farnesylated, in the presence of the protein prenyl transferase inhibitor, it cannot effect interaction of the ras protein with the membrane so that neoplastic transformation of the cell will be prevented. In this manner proteinprenyl transferase inhibitors prevent neoplastic transformation of the cell, thereby acting as an anti-cancer agent for the treatment of and/or prevention of ras-related tumors.

Examples of CAAX box containing proteins which have been demonstrated or are believed to undergo prenylation include, but are not limited to, ras, nuclear lamins, α or γ subunits of heterotrimeric G-proteins, γ-subunits of retinal transducin, G25K and K-rev p21, and protein families including rho, rap, rac, ral, and rab.

The present invention includes a method for blocking or preventing the prenylation of CAAX box containing proteins such as ras oncogene products, and thereby inhibit disease promoting effects of the CAAX box containing protein or more specifically prevent and/or treat ras-related tumors, by administering to a patient in need of treatment a therapeutic amount of a compound of Formula I of the invention which serves as a protein-prenyl transferase inhibitor.

The Formula I protein-prenyl transferase inhibitors, unlike HMG CoA reductase inhibitors, will interfere with prenylation of the ras oncogene products and inhibit their transforming activity, yet may or may not interfere with the synthesis of FPP, a precursor in the synthesis of ubiquinones, dolichols and Haem A.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin.

The above compounds to be employed in combination with the squalene synthetase inhibitor of the invention will be used in amounts as indicated in the Physicians' Desk Reference (PDR).

The compounds of the invention may also be employed with sodium lauryl sulfate of other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

A further aspect of the present invention is a pharmaceutical composition consisting of at least one of the compounds of the invention, such as Formula I, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc., by an oral route, for example, in the form of tablets, capsules, granules or powders, or they can be administered by a parenteral route in the form of injectable preparations. The dose for adults is preferably between 20 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectible preparation is produced by asceptically placing 250 mg of sterile active ingredient into a vial, aseptically freeze-drying and sealing. For use, the contents of the vial are mixed with 2 mL of physiological saline, to produce an injectible preparation.

The following Examples represent preferred embodiments of the present invention.

INTRODUCTION TO EXPERIMENTAL

All temperatures are reported in degrees Centigrade.
$^1$H and $^{13}$C chemical shifts are reported as δ-values with respect to Me$_4$Si (δ=0).

All reactions were carried out under an atmosphere of dry argon or nitrogen. The following reagents and solvents were distilled prior to use from the indicated drying agents, where applicable: $CH_2Cl_2$, 2,4,6-collidine, and diisopropylamine ($CaH_2$); THF and diethyl ether (K, benzophenone); N,N-diethyltrimethylsilylamine and oxalyl chloride. Benzene was passed through a neutral alumina (activity I) and stored over 4A-molecular sieves. Lithium bromide was dried at 100° C. over $P_2O_5$. (E,E)-Farnesol was purchased from Aldrich Chemical Company.

TLC was performed on E. Merck Silica Gel 60 F-254 plates (0.25 mm) or E. Merck Cellulose F plates (0.1 mm). Flash chromatography was carried out using E. Merck Kieselgel 60 (230-400 mesh).

Reverse-phase chromatographic purification of salts or mixed ester salts was carried on CHP20P gel or SP207SS gel, highly porous, polystyrene-divinyl benzene copolymers available from Mitsubishi Chemical Industries. The indicated general procedure was followed: An FMI Model RP-SY pump was utilized for solvent delivery. A column of CHP20P or SP207SS (2.5 cm diameter, 12-22 cm height) was slurry packed and washed with water (500-1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300-500 mL of the organic solvent, or an aqueous-organic mixture, just beneath the surface of a reservoir containing 300-500 mL of pure water. To start the gradient, the topcock of the separatory funnel was opened, so that as the solvent was withdrawn by the pump from the reservoir, it was replaced with the solvent from the separatory funnel. HPLC-grade solvents were employed. Fractions were collected (10-15 mL each) at a flow rate of 5-10 mL per minute. Those fractions that contained pure product as judged by TLC or HPLC were pooled, the organic solvents were evaporated and the aqueous residue was lyophilized to dryness.

EXAMPLE 1

(E,E)-7,11,15-Trimethyl-2-phosphono-6,10,14-hexadecatrienoic acid, trisodium salt (SQ32,783)

A. Bishomofarnesol (1) (E,E)-3,7,11,-Trimethyl-2,6,10-dodecatrienyl bromide (farnesyl bromide)

A solution of 1.00 g (4.5 mmol) of (E,E)-farnesol (Aldrich, further purified by flash chromatography) in 10 mL of distilled ether at 0° C. under argon in the dark was treated dropwise with a solution of 195 μL (2.05 mmol, 0.45 eq.) of $PBr_3$ in 2 mL of diethyl ether (ether). The resultant mixture was stirred at 0° C. for one hour, then quenched with water and separated. The organic phase was washed with 5 mL of $H_2O$, 5 mL of saturated $NaHCO_3$, and 5 mL of brine, dried over $Na_2SO_4$ and evaporated to give 1.26 g (98%) of crude bromide as a clear oil.

TLC Silica (2:8 ethyl acetate:hexane) $R_f=0.69$.

$^1H$ NMR ($CDCl_3$, 270 MHz): δ 5.52 (t, 1H, J=8.5 Hz) 5.08 (m, 2H) 4.01 (d, 2H, J=8.5 Hz) 2.20-1.90 (m, 8H) 1.73 (s, 3H) 1.68 (s, 3H) 1.60 (s, 6H) ppm.

(2) (E,E)-5,9,13-Trimethyl-4,8,12-tetradecatrienoic acid, 1.1-dimethylethyl ester To a solution of 9.60 mL (68.5 mmol, 1.5 eq.) of diisopropylamine in 100 mL of tetrahydrofuran (THF) at −78° C. under argon was added 28.2 mL (45.0 mmol, 1.0 eq.) of 1.6M n-butyllithium in hexanes over 20 minutes. After warming to 0° C. for 15 minutes, the solution was recooled to −78° C. and 6.05 mL (45 mmol, 1.0 eq.) of t-butyl acetate was added over 20 minutes. After an additional 15 minutes, 16.0 mL (92 mmol, 2.05 eq.) of hexamethylphosphoramide (HMPA) was added, followed by a solution of 12.53 g (45.0 mmol) of Part A(1) farnesyl bromide in 100 mL of THF over 20 minutes. The reaction was stirred at −78° C. for 2.5 hours, quenched with saturated $NH_4Cl$ and allowed to warm to room temperature. After diluting with 400 mL of ethyl acetate, the mixture was washed with four 100 mL portions of water, and 200 mL of brine, dried over $MgSO_4$ and evaporated to provide 12.96 g of crude product as a yellow oil. Purification by flash chromatography on 1 kg of silica gel, eluted with 1:9 ethyl acetate:petroleum ether afforded 9.39 g (65%) of title compound as a pale yellow oil.

TLC Silica gel (2:98 ethyl acetate:hexane) $R_f=0.16$.

IR(neat) 2977, 2925, 2857, 1733, 1452, 1368, 1258, 1149 $cm^{-1}$.

$^1H$ NMR($CDCl_3$, 270 MHz): δ 5.10 (m, 3H) 2.25 (m, 4H) 2.10-1.90 (m, 8H) 1.68 (s, 3H) 1.62 (s, 3H) 1.59 (s, 6H) 1.44 (s, 9H) ppm.

Mass spec. (CI-$CH_4/N_2O$) (+ions) m/e 265 (M+H-$C_4H_8$), 247, 183, 137, 68, 67. (−ions) m/e 319 (M−H), 279, 251, 100.

(3) Bishomofarnesol

To a stirred solution of 5.00 g (15.6 mmol) of Part (2) compound in 45 mL of dry diethyl ether at 0° C. under argon was added 592 mg (15.6 mmol, 1 mol - eq.) of lithium aluminum hydride, and the resulting suspension was stirred at room temperature for 20 hours. After cooling to 0° C., the reaction was quenched by treating with 5 mL of $H_2O$, 5 mL of 15% NaOH, and 15 mL of $H_2O$ and stirring the suspension for ½ hour. After adding $Na_2SO_4$, the slurry was filtered through Celite, washing well with diethyl ether and evaporated to obtain 3.62 g of crude product. Purification by flash chromatography on 300 g of silica gel, eluted with 1:9 ethyl acetate:petroleum ether provided 3.52 g (90%) of bishomofarnesol as a colorless liquid.

TLC Silica gel (2:8 ethyl acetate:hexane) $R_f=0.19$.

IR(neat) 3330, 2964, 2926, 2873, 2958, 1448, 1384, 1107, 1059, 401 $cm^{-1}$.

$^1H$ NMR($CDCl_3$, 270 MHz): δ 5.10 (m, 3H) 3.63 (t, 2H, J=6.5 Hz) 1.9-2.2 (m, 10H) 1.68 (s, 3H) 1.62 (s, 3H) 1.60 (s, 7H) ppm.

Mass Spec (CI-$CH_4/N_2O$, +ions) m/e 251 (M+H).

$A^1$. Bishomofarnesol (alternative preparation)

(1)

(E,E)-(3,7,11-Trimethyl-2,6,10-undecadienyl)-propanedicarboxylic acid, diethyl ester To a suspension of 1.62 g (40.5 mmol, 3 eq.) of a 60% suspension of sodium hydride in mineral oil (washed three times with pentane) in 150 mL of tetrahydrofuran at room temperature under argon was slowly added 6.15 mL (40.5 mmol, 3 eq.) of diethyl malonate. The resulting solution was stirred for 0.5 hours, then treated with a solution of 3.83 g (13.5 mmol) of farnesyl bromide in 10 mL of tetrahydrofuran. After stirring for 6 hours, the reaction was quenched with saturated $NH_4Cl$ and diluted with 300 mL of diethyl ether. The organic layer was washed with two 100 mL portions of water and 100 mL of brine, dried over MgSO₄ and evaporated and the bulk of the diethyl malonate removed by spinning under high vacuum to afford 4.29 g (87%) of crude title product.

TLC Silica gel (1:9 ethyl acetate:hexane) $R_f$=0.37.

(2) (E,E)-5,9,13-Trimethyl-4,8,12-tetradecatrienoic acid, ethyl ester

A mixture of 4.10 g (11.2 mmol) of Part A¹ (1) diester, 200 μL (11.2 mmol, 1 eq.) of water and 950 mg (22.4 mmol, 2 eq.) of lithium chloride in 20 mL of dimethyl sulfoxide was heated at reflux (~190° C.) for four hours. After cooling, the reaction mixture was diluted with 180 mL of a 1:1 mixture of diethyl ether:petroleum ether and washed with five 50 mL portions of water and 50 mL of brine, dried over MgSO₄ and evaporated to yield 3.62 g of crude product as a yellow-orange oil. Kugelrohr distillation at 180° C. (meter setting) and 0.025 mm allowed the collection of 2.10 g of a pale yellow oil, which was, however, still contaminated (by TLC). The distillation, therefore, is unnecessary and should not be performed. Flash chromatography on 180 g of silica gel, eluted with 3:97 ethyl acetate:petroleum ether provided 1.84 g (56%) of desired title product as a pale yellow oil.

TLC Silica gel (5.95 ethyl acetate:hexane) $R_f$=0.27.

¹H-NMR (CDCl₃, 270 MHz): δ 5.08 (m, 3H) 4.12 (q, 2H, J=6.7 Hz) 2.31 (m, 4H) 2.10–1.90 (m, 8H) 1.67 (s, 3H) 1.62 (s, 3H) 1.59 (s, 6H) 1.25 (t, 3H, J=6.7 Hz) ppm.

(3) Bishomofarnesol

A solution of 7.05 g (24 mmol) of Part A¹ (2) monoester in 65 mL of dry diethyl ether at 0° C. under argon was treated in portions with 915 mg (24 mmol) of lithium aluminum hydride and stirred at room temperature for three hours, After cooling to 0° C., the reaction was quenched with 7 mL of water, 7 mL of 15% NaOH, then stirred for 15 minutes. Additional 21 mL of water was added, and the reaction was stirred 0.5 hours, then dried with Na₂SO₄. The mixture was filtered through Celite, washing well with diethyl ether, and evaporated to give 5.665 g of a colorless oil. Purification by flash chromatography on silic gel eluted with 15:85 ethyl acetate:petroleum ether provided 5.23 g (87%) of title compound as a colorless oil.

TLC Silica gel (2:8 ethyl acetate:hexanes) $R_f$=0.21.

IR(neat) 3330, 2964, 2926, 2873, 2858, 1448, 1384, 1107, 1059, 401 cm⁻¹.

¹H-NMR (CDCl₃, 270 MHz): δ 5.10 (m, 3H) 3.63 (t, 2H, J=6.5 Hz) 2.20–1.90 (m, 10H) 1.68 (s, 3H) 1.62 (s, 3H) 1.60 (s, 6H) ppm.

Mass Spec (CI-CH₄/N₂O, +ions) m/e 251 (M+H).

B. (E,E)-5,9,13-Trimethyl-4,8,12-tetradecatrien-1-ol, methanesulfonate ester To a stirred solution of 2.02 g (8.07 mmol) of bishomofarnesol (prepared as described in Example 1, Part A) in 20 mL of dichloromethane at 0° C. was added 2.2 mL (16.1 mmol) of triethylamine followed by 0.69 mL (8.90 mmol) of methanesulfonyl chloride, dropwise over 15 mintues. After stirring for 1.5 hours at 0° C., the reaction was diluted with dichloromethane, washed with 20 mL each of 10% HCl, saturated NaCHO₃ and brine, dried (MgSO₄) and evaporated to give 2.71 g (100%) of the crude title mesylate as a colorless oil.

TLC Silica gel (CH₂Cl₂) $R_f$=0.46.

¹H NMR (CDCl₃, 270 MHz): δ 5.09 (t, 3H, J=6.5 Hz) 4.21 (t, 2H, J=7.0 Hz) 2.99 (s, 3H) 2.20–1.90 (m, 10H) 1.78 (quint, 2H, J=7.0 Hz) 1.65 (s, 3H) 1.61 (s, 3H) 1.60 (s, 6H), ppm.

C. (E,E)-14-Iodo-2,6,10-trimethyl-2,6,10-tetradecatriene

The crude Example 1, Part B mesylate prepared from 441.1 mg (1.76 mmol) of the corresponding alcohol according to the procedure of Example 1, Part B, was dissolved in 5 mL of acetone and treated with 530 mg (3.52 mmol) of sodium iodide. The reaction was allowed to stir for 16 hours at room temperature followed by 5 hours at reflux. The suspension was diluted with hexane and stirred with dilute aqueous sodium disulfite to discharge to yellow color. The organic layer was washed with water and brine, dried (MgSO₄), and evaporated to provide 577 mg of crude product. Flash chromatography on 35 g of silica gel eluted with hexane gave 550.9 mg (87%) of title iodide as a colorless liquid.

TLC Silica gel (hexane) $R_f$=0.31.

¹H NMR (CDCl₃, 270 MHz): δ 5.09 (m, 3H) 3.16 (t, 2H, J=7.0 Hz) 2.20–1.90 (m, 12H) 1.85 (quint., 2H, J=6.5 Hz) 1.67 (s, 3H) 1.63 (s, 3H) 1.59 (s, 6H) ppm.

Mass Spec (CI-CH₄/N₂O, +ions) m/e 361, 359 (M+H).

D. (E,E)-2-(Diethoxyphosphinyl)-7,11,15-trimethyl-6,10,14-hexadecatrienoic acid, ethyl ester To a stirred solution of 400 mg (16.60 mmol) of NaH in 30 mL of THF at 0° C. under argon was added 3.10 mL (16.60 mmol) of triethylphosphonoacetate over 0.5 h. The mixture was stirred for 0.5 h at 0° C. and then was treated with 2.0 g (5.60 mmol) of Part C iodide over 0.2h. The reaction stirred at 0° C. for 2 h, then at RT for 20 h, at which time it was diluted with 200 mL of Et₂O and quenched with 100 mL of NH₄Cl. The organic layer was washed with water, brine and dried over MgSO₄. The solvent was evaporated to provide 2.36 g of a crude yellow oil. Flash chromatography was performed on 100 g of silica gel, packed, loaded and eluted with 60:40 Hexane: EtOAc. Pure product fractions were combined and evaporated to provide 1.69 g (68%) of title compound as a pale yellow oil.

TLC Silica gel (90:10 hexane:EtOAc) $R_f$=0.79.

¹H NMR (270 MHz, CDCl₃): δ 5.10 (t, 3H, J=5.8 Hz) 4.30–4.10 (m, 6H) 2.95 (ddd, 1H, J=22.3, 10.5, 4.1 Hz) 2.20–1.80 (m, 12H) 1.67 (s, 3H) 1.59 (s, 9H) 1.45–1.20 (m, 11H) ppm.

E. (E,E)-2-(Diethoxyphosphinyl)-7,11,15-trimethyl-6,10,14-hexadecatrienoic acid To a stirred solution of 1.1 g (2.40 mmol) of Part D compound in 10 mL of ethanol at RT under argon was added 10 mL (3.60 mmol) of NaOH. This mixture was heated to 55° C. for 20 h, cooled to RT, acidified with KHSO₄ and extracted with EtOAc. The organic layer was dried over MgSO₄ and evaporated to yield 1.02 g of a clear oil. The residue was used in the next step without further purification.

TLC Silica gel (8:1:1 n-propanol:conc. NH₃:H₂O) $R_f$=0.64.

¹H NMR (270 MHz, CDCl₃): δ 5.13–5.06 (m, 3H) 4.19–4.08 (m, 4H) 2.80 (ddd, 1H, J=3.7, 10.7, 21.7 Hz) 2.07–1.95 (m, 12H) 1.66 (s, 3H) 1.61 (s, 6H) 1.58 (s, 6H) 1.40 (m, 2H) 1.31 (t, 6H, J=7.04 Hz) ppm.

F. (E,E)-7,11,15 Trimethyl-2-phosphono-6,10,14-hexadecatrienoic acid, trisodium salt To a stirred solution of 1.02 g (2.40 mmol) of Part E compound in 10 mL of $CH_2Cl_2$ at RT under argon was added 951 μL (7.20 mmol) of 2,4,6-collidine followed by 1.42 mL (10.80 mmol) of bromotrimethylsilane. The mixture was stirred at RT for 20 h, at which time the solvent was evaporated and pumped on at high vacuum for 20 min. The remainder was dissolved in 17.3 mL (8.65 mmol) of 0.5M NaOH and lyophilized. The crude material was purified by MPLC on a column of CHP20P (2.5 cm diameter × 17.5 cm height) eluted with water (fraction 1 to 10) followed by a gradient created by the gradual addition of 350 mL of $CH_3CN$ to a reservoir of 350 mL of water. Approximately 15 mL fractions were collected. Pure product fractions were combined, evaporated to remove $CH_3CN$ and lyophilized to provide 816 mg (78%) of title salt as a white lyophilate.

TLC Silica gel (5:4:1 n-propanol:conc. $NH_3:H_2O$) $R_f=0.37$.

IR (KBr): 3440, 3432, 3060, 3054, 3033, 3028, 2966, 2925, 2856, 1635, 1558, 1442, 1390, 1163, 1089, 975 $cm^{-1}$.

$^1H$ NMR (400 MHz, $D_2O$): δ 5.23 (t, 1H, J=6.8 Hz) 5.11 (q, 2H, J=6.6Hz) 2.46 (ddd, 1H, J=2.93, 13.4, 24.3 Hz) 2.05-1.96 (m, 10H) 1.70 (m, 2H) 1.63 (s, 3H) 1.57 (s, 9H) 1.25 (m, 2H) ppm.

Mass Spec (FAB, +ions) m/e 461 (M+Na), 439 (M+H), 417 (M+2H-Na).

Anal. calc'd for $C_{19}H_{30}PO_5Na_3 + 1.01\ H_2O$: C, 49.98; H, 7.07; P, 6.78. Found: C, 50.06; H, 7.21; P, 6.96.

EXAMPLE 2

2-(Dihydroxyphosphinyl)-3-[(3,7,11-trimethyl-2,6,10-dodecatrienyl)oxy]propanoic acid, trisodium salt

A. Allyl-12-bromopropionate

To a solution of 34.0 mL (0.5 mmol, 1 eq.) of allyl alcohol and 44.0 mL (0.55 mol, 1.1 eq.) of dry pyridine in 150 mL of $CH_2Cl_2$ at 0° C. under $N_2$ was added over one hour a solution of 52.5 mL (0.5 mol, 1 eq.) of 2-bromopropionyl bromide (Aldrich, and used without further purification) in 50 mL of $CH_2Cl_2$. The suspension was allowed to warm to room temperature and continued stirring for 12 hours. After removal of precipitated salts by filtration, the filtrate was washed with three 50 mL portions of 10% HCl and two 50 mL portions of saturated $NH_4Cl$, dried over $MgSO_4$ and evaporated. Purification by fractional distillation provided 75.54 g (78%) of title compound at 53–54° C./5mm.

$^1H$-NMR($CDCl_3$) (270 MHz) δ 5.93 (ddt, 1H, J=17.2, 10.3, 5.8 Hz) 5.39 (dd, 1H, J=17.2, 1.6, Hz) 5.28 (dd, 1H, J=10.3, 1.6 Hz) 4.66 (dq, 2H, J=5.8, 1.5 Hz) 4.40 (q, 1H, J=6.9 Hz) 1.84 (d, 3H, J=6.9 Hz) ppm.

B. Triallyl 2-phosphonopropionate

A mixture of 20.02 g (104 mmol) of Part A allyl-2-bromopropionate and 43 mL (312 mmol, 3 eq.) of triallylphosphite (Aldrich, purified by distillation) under nitrogen was warmed over one hour to ~160° C. and stirred for three hours. After cooling, the product mixture was purified by fractional distillation. The portion collected at 105°–108° C./0.1 mm was again subjected to fractional distillation. providing 9.55 g (33%) of desired phosphonate, bp 93°–95° C./0.05 mm.

TLC Silica gel (8:2 ethyl acetate:hexane) $R_f$ 0.37.

IR($CCl_4$) 3100, 3000, 2950, 2900, 1741, 1457, 1311, 1290, 1263, 1168, 1097, 1019, 992, 932, $cm^{-1}$.

$^1H$-NMR ($CDCl_3$) (270 MHz) δ 5.8–6.0 (m, 3H) 5.35 (d, 3H, J=18.4 Hz) 5.24 (d, 3H, J=10.6 Hz) 4.5–4.7 (m, 6H) 3.11 (dq, 1H, J=23.7, 7.4 Hz) 1.48 (ddd, 3H, J=18.5, 7.4, 1.1 Hz) ppm.

Mass Spec ($CI-CH_4/N_2O$+ions) m/e 315 (M+$C_3H_5$), 303 (M+$C_2H_5$), 275 (M+H).

C. 2-[Bis(2-propenyloxy)phosphinyl]-2-(phenylselenyl)-propanoic acid. 2-propenyl ester A solution of 2.90 g (10.6 mmol) of Part B triallyl 2-phosphonopropionate in 50 mL of tetrahydrofuran at −78° C. under argon was treated with 11.7 mL (11.7 mmol 1.1 eq) of a 1.0M solution of lithium bis(trimethylsilyl)amide in tetrahydrofuran. After 0.5 hours, 2.23 g (11.7 mmol, 1.1 eq) of phenylselenyl chloride was added. The reaction was stirred three hours at −78° C., then warmed to room temperature and stirred for two hours. After quenching with saturated $NH_4Cl$ and diluting with 150 mL of diethyl ether, the separated organic layer was washed with 30 mL of $H_2O$ and 30 mL of brine, dried over $MgSO_4$ and evaporated to give 4.19 g of an orange oil. Three flash rechromatographic columns were required to purify the product. Column I was on 200 g Merck 9385 silica eluted with 3:7 ethyl acetate:petroleum ether to yield 2.11 g of impure product and 1.16 g (26%) of pure product. The impure fractions were rechromatographed on 200 g Merck silica, eluting with 2:8 diethyl ether): toluene to obtain 1.03 g of still impure title compound. A final chromatography on 70 g of Merck 9385 silica, eluted with 3:7 ethyl acetate: petroleum ether provided an additional 859 mg (19%) of pure product for a combined total of 2.02 g (45%) of title selenide as a pale yellow oil.

TLC Silica gel (4:6 ethyl acetate:hexane) $R_f$ 0.27.

$^1H$-NMR ($CDCl_3$) (270 MHz) δ 7.68 (d, 2H, J=7.1 Hz) 7.40 (t, 1H, J=7.1 Hz) 7.30 (t, 2H, J=7.1 Hz) 6.00 (m, 2H) 5.80 (m, 1H) 5.30 (m, 6H) 4.60(m, 6H) 1.60 (d, 3H, J=15.4 Hz) ppm.

D. 2-[Bis(2-propenyloxy)phosphinyl]-2-propenoic acid, 2-propenyl ester

A solution of 1.30 g (3.02 mmol) of Part C phenylselenide in 9 mL of $CH_2Cl_2$ at 0° C. under argon was treated with 1.03 mL (9.07 mmol, 3 eq) of 30% $H_2O_2$ in 1.0 mL of $H_2O$. The reaction was allowed to stir for 45 minutes, then diluted with 40 mL of $CH_2Cl_2$ and separated. The organic phase was washed with 5 mL of 10% $Na_2CO_3$ and 5 mL of brine, dried over $MgSO_4$ and evaporated to obtain 730 mg (89%) of title acrylate.

TLC Silica gel (4:6 ethyl acetate:hexane) $R_f$ 0.21.

IR ($CCl_4$) 3090, 2950, 2890, 1731, 1267, 1174, 1134, 1099, 1018, 990, 933 $cm^{-1}$.

$^1H$-NMR($CDCl_3$) (270 MHz) δ 6.99 (dd, 1H, J=42.3, 1.1 Hz) 6.78 (dd, 1H, J=20.3, 1.1 Hz) 5.8–6.0 (m, 3H) 5.2–5.5 (m, 6H) 4.72 (dd, 2H, J=5.5, 1.1 Hz) 4.5–4.7 (m, 4H) ppm.

Mass Spec. ($CI-CH_4$+ions) m/e 313 (M+$C_3H_5$), 301 (M+$C_2H_5$), 273 (M+H).

E. (E,E)-2-[Bis(2-propenyloxy)phosphinyl]-3-[(3,7,11-trimethyl-2,6,10-dodecatrienyl)oxy]propanoic acid, 2-propenyl ester To 0.6 mL (2.3 mmol, 2.6 eq) of farnesol and purified by preparative MPLC chromatography prior to use) at room temperature under argon was added a solution of 236 mg (0.88 mmol) of Part D acrylate in 0.5 mL (2.1 mmol, 2.4 eq) of farnesol. The reaction was allowed to stir overnight and purified by flash chromatography on 70 g of Merck 9385 silica, eluting with 25:75 ethyl acetate:hexanes to obtain 290.7 mg (45%) of pure title compound as a clear, colorless oil.

TLC Silica gel (4.6 ethyl acetate:hexanes) $R_f$ 0.27.

IR (CCl$_4$) 2967, 2927, 2882, 2857, 1742, 1452, 1266, 1160, 1097, 1030, 1016, 990, 932 cm$^{-1}$.

$^1$H-NMR(CDCl$_3$) (270 MHz) δ 5.8–6.0 (m, 3H) 5.2–5.4 (m, 7H) 5.09 (m, 2H) 4.67 (dd, 2H, J=5.6, 1.3 Hz) 4.59 (m, 4H) 4.00 (d, 2H, J=6.3 Hz) 3.95 (m, 1H) 3.84 (ddd, H1, J=10.0, 6.9, 4.2 Hz) 3.42 (ddd, 1H, J=22.7, 10.0, 4.2 Hz) 1.9–2.2 (m, 8H) 1.68 (s, 3H) 1.65 (s, 3H) 1.60 (s, 6H) ppm.

Mass Spec (CI-CH$_4$/N$_2$O, −ions) m/e 493 (M−H), 453, 272.

F.
2-(Dihydroxyphosphinyl)-3-[(3,7,11-trimethyl-2,6,10-dodecatrienyl)oxy]propanoic acid, trisodium salt A solution of 171.2 mg (0.35 mmol) of Part E triester in 4 mL of tetrahydrofuran at room temperature under argon was treated with 640 μL (4.85 mmol, 14 eq) of dimethylethylsilane, followed by 61.3 mg (0.05 mmol, 0.15 eq) of tetrakis(triphenylphosphine)palladium and 82.5 mg (0.32 mmol, 0.9 eq) of triphenylphosphine. The mixture was allowed to stir six hours in the dark, then added to a mixture of 1.05 mL (1.05 mmol, 3 eq) of 1M NaOH, 1.0 mL H$_2$O and 2.0 mL methanol at 0° C. After 0.5 hours, the mixture was adjusted to pH 13 with 1M NaOH, diluted with 20 mL of H$_2$O and filtered through Celite. The organic solvents were evaporated and the remaining aqueous solution was lyophilized. The crude product was purified by chromatography on 2.5 cm diameter×8 cm height column of CHP-20P resin loaded in water. The column was eluted with 100 mL of H$_2$O followed by a gradient created by the gradual addition of 300 mL of 1:1 CH$_3$CN:H$_2$O into 300 mL of H$_2$O. Approximately 8 mL fractions were collected every 1.5 minutes. Fractions 47–53 were combined, filtered, evaporated and lyophilized overnight to provide 75.5 mg (46%) of title salt as a flocculate, white lyophilate.

TLC Silica gel (6:3:1 nC$_3$H$_7$OH: con. NH$_3$:H$_2$O) $R_f$ 0.16.

IR (KBr) 3000–3700(br) 2967, 2923, 2859, 1666, 1574, 1449, 1393, 1159, 1103, 978, 583, 499 cm$^{-1}$.

$^1$H NMR (D$_2$O) (400 MHz) δ 5.37 (t, 1H, J=6.8 Hz) 5.18 (t, 1H, J=7.0 Hz) 5.16 (t, 1H, J=7.0 Hz) 3.9–4.1 (m, 3H) 3.77 (ddd, 1H, J=10.3, 4.0, 3.0 Hz) 2.90 (ddd, 1H, J=22.0, 11.4, 3.0 Hz) 2.0–2.2 (m 6H) 2.00 (t, 2H, J=7.2 Hz) 1.67 (s, 6H) 1.60 (s, 6H) ppm.

$^{31}$P-NMR (D$_2$O) (36.2 MHz) δ 14.50 ppm.

($^{31}$P-NMR was accumulated in a proton-decoupled mode with 85% H$_3$PO$_4$ as an external reference).

Mass Spec (FAB, +ions) m/e 463 (M+Na), 441 (M+H), 419 (M+2H−Na).

Anal. calc'd for C$_{18}$H$_{28}$O$_6$P 3Na+2.10 H$_2$O: C, 45.21; H, 6.79; P, 6.48. Found: C, 45.21; H, 6.76; P, 6.58.

EXAMPLE 3
(E,E)-2-(Dihydroxyphosphinyl)-4-[(3,7,11-trimethyl-2,6,10-dodecatrienyl)oxy]butanoic acid, trisodium salt A.
(E,E)-1-(2-Iodoethoxy)-11-methyl-2,6,10-dodecatriene A(1).
(E,E)-[(3,7,11-Trimethyl-2,6,10-dodecatrienyl)oxy]acetic acid, methyl ester To a suspension of 3.60 g (90 mmol, 2 equiv) of 60% NaH in mineral oil, washed three times with pentane, in 170 mL of tetrahydrofuran at room temperature under argon was added a solution of 10.00 g (45 mmol) of E,E-farnesol in 30 mL of tetrahydrofuran, and the resulting mixture was heated at reflux for 0.5 hours. After having cooled to room temperature the reaction was treated with 1.66 g (4.5 mmol, 10%) of tetra-n-butylammonium iodide and 5.50 g (47.5 mmol, 1.05 eq.) of the sodium chloroacetate, and heated to reflux for 20 hours. The mixture was cooled to 0° C. and 200 mL of dimethylformamide was slowly added, followed by 9.4 mL (99 mmol, 2.2 eq.) of dimethylsulfate. After four hours, the reaction was diluted with 600 mL of 1:1 diethyl ether:hexane, washed with five 100 mL portions of H$_2$O and 100 mL of brine, dried over MgSO$_4$, and evaporated to afford 14.09 g of a dark yellow oil. Purification by flash chromatography on 1000 g of Merck 9385 silica, eluted with 5:95 ethyl acetate:hexane provided 10.19 g (77%) of title ester as a yellow oil.

TLC: Silica gel (2:8 ethyl acetate:hexane) $R_f$ 0.36.

IR (CCl$_4$) 2966, 2949, 2917, 2854, 1759, 1742, 1438, 1380, 1278, 1204, 1129, 1025, 992, 938, cm$^{-1}$.

$^1$H-NMR (CDCl$_3$) (270 MHz) δ 5.36 (t, 1H, J=7.2 Hz) 5.09 (m, 2H) 4.11 (d, 2H, J=7.2 Hz) 4.06 (s, 2H) 3.75 (s, 3H) 2.20–1.90 (m, 8H) 1.68 (s, 6H) 1.60 (s, 6H) ppm.

Mass Spec (EI, +ions) 294 (M.), 204, 189, 157, 136, 69.

A(2).
(E,E)-2-[(3,7,11-Trimethyl-2,6,10-dodecatrienyl)oxy]ethanol

A solution of 1.50 g (5.09 mmol) of Part A(1) ester in 20 mL of diethyl ether at 0° C. under argon was treated with 197.1 mg (5.09 mmol, 1 mol equiv) of lithium aluminum hydride and stirred at 0° C. for one hour. The reaction was cautiously quenched by adding successively 0.2 mL of H$_2$O, 0.2 ml of 15% NaOH and 0.6 mL of H$_2$O, stirring 15 minutes, then adding Na$_2$SO$_4$ and stirring 0.5 hours. After filtering through Celite, the solution was evaporated to give 1.47 g of a pale yellow oil. Purification by flash chromatography on 70 g of Merck 9385 silica, eluted with 2:8 ethyl acetate:hexane, afforded 1.065 g (85%) of title alcohol as a clear, colorless oil.

TLC: Silica gel (3:7 ethyl acetate:hexane) $R_f$ 0.24.

IR (CCl$_4$) 3604, 3470, (br), 2966, 2923, 2858, 1668, 1449, 1382, 1363, 1114, 1055, 1026, 988, 890 cm$^{-1}$.

$^1$H-NMR (CDCl$_3$) (270 MHz) δ 5.36 (t, 1H, J=6.5 Hz) 5.11 (m, 2H) 4.05 (d, 2H, J=6.5 Hz) 3.73 (t, 2H, J=4.5 Hz) 3.53 (t, 2H, J=4.5 Hz) 2.28 (br; 1H, OH) 2.20–1.90 (m, 8H) 1.68 (s, 6H) 1.60 (s, 6H) ppm.

Mass Spec (CI-CH$_4$/N$_2$O, +ions) m/e 267 (M+H), 265 (M+H−H$_2$), 205, 137.

A(3).
(E,E)-1-(2-Iodoethoxy)-11-methyl-2,6,10-dodecatriene

The mesylate was prepared by treating a solution of 1.081 g (3.75 mmol) of Part A(2) alcohol in 10 mL of $CH_2Cl_2$ at 0° C. under argon with 1.05 mL (7.5 mmol, 2 equiv.) of triethylamine and dropwise with 320 μL (4.13 mmol, 1.1 equiv.) of methanesulfonyl chloride. After three hours an additional portion of 60 μL (0.75 mmol, 0.2 eq.) of methanesulfonyl chloride was added. The reaction was stirred 0.5 hours, then diluted with 30 mL of $CH_2Cl_2$ and washed with 10 mL of 1M HCl, 10 mL of $NaHCO_3$, 10 mL of $H_2O$ and 10 mL of brine, dried over $MgSO_4$ and evaporated to obtain 1.29 g ("100%") of intermediate mesylate.

TLC: Silica gel (4:6 ethyl acetate:hexane) $R_f$ 0.36.

$^1$H-NMR ($CDCl_3$) (270 MHz) δ 5.32 (t, 1H, J=6.9 Hz) 5.10 (m, 2H) 4.36 (t, 2H, J=4.5 Hz) 4.05 (d, 2H, J=6.9 Hz) 3.68 (t, 2H, J=4.5 Hz) 3.05 (s, 3H) 2.20-1.90 (m, 8H) 1.68 (s, 6H) 1.60 (s, 6H) ppm.

A solution of 1.30 g (3.75 mmol) of mesylate and 1.13 g (7.50 mmol, 2 eq.) of sodium iodide in 10 mL of acetone under argon was heated at reflux for six hours. The mixture was diluted with 40 mL of hexane, washed with two 5 mL portions of $H_2O$ and 5 mL of brine, dried over $MgSO_4$ and evaporated to yield 1.21 g of crude alcohol. Purification by flash chromatography on 70 g of Merck 9385 silica, eluted with 2.5:97.5 ethyl acetate:hexane afforded 1.096 g (78%) of title iodide.

TLC: Silica gel (5:95 ethyl acetate:hexane) $R_f$ 0.14.

B.
(E,E)-2-(Diethoxyphosphinyl)-4-[(3,7,11,-trimethyl-2,6,10-dodecatrienyl)oxy]butanoic acid, ethyl ester To a suspension of 363 mg (9.0 mmol, 3 equiv) of 60% NaH suspension in mineral oil (washed three times with pentane) in 6 mL of tetrahydrofuran at room temperature under argon was added dropwise 1.80 mL (9.0 mmol, 3 equiv) of triethylphosphonoacetate over ten minutes. After 0.5 hours, a solution of 1.16 g (3.0 mmol) of Part A iodide in 9 mL of tetrahydrofuran was added over ten minutes. The reaction mixture was allowed to stir for 48 hours at room temperature and for 24 hours at reflux. After cooling, the solution was diluted with 20 mL of diethyl ether and quenched with saturated $NH_4Cl$. The mixture was extracted with 75 mL of diethyl ether and the separated organic phase was washed with 10 mL of water and 10 mL of brine, dried over $MgSO_4$ and evaporated to yield 1.73 g of an orange oil. The crude product was purified by three successive flash chromatographies on silica gel, the final being eluted with 12:88 acetone:hexane to provide 357 mg (25%) of title compound as a colorless oil.

TLC Silica gel (3:7 acetone:hexane) $R_f$ 0.27.

IR ($CCl_4$) 2981, 2930, 2913, 2857, 1735, 1443, 1369, 1329, 1257, 1174, 1160, 1107, 1098, 1055, 1028, 968 cm$^{-1}$.

$^1$H-NMR ($CDCl_3$) (270 MHz) δ 5.30 (t, 1H, J=6.6 Hz) 5.10 (m, 2H) 4.16 (m, 6H) 3.94 (d, 2H, J=6.6 Hz) 3.44 (m, 2H) 3.16 (ddd, 1H, J=23.1, 10.4, 3.8 Hz) 2.30-1.90 (m, 10H) 1.68 (s, 3H) 1.65 (s, 3H) 1.60 (s, 6H) 1.33 (dt, 6H, J=2.2, 6.8 Hz) 1.29 (t, 3H, J=6.8 Hz) ppm.

Mass Spec (CI-$CH_4$/$N_2O$+ions) m/e 501 (M+$C_2H_5$), 473 (M+H) 269, 251.

C.
(E,E)-2-(Diethoxyphosphinyl)-4-[(3,7,11-trimethyl-2,6,10-dodecatrienyl)oxy]butanoic acid A mixture of 268 mg (0.60 mmol) of Part B triester in 1 mL of $H_2O$ and 1.5 mL of ethanol was treated with 660 μL (0.66 mmol, 1.1 equiv) of 1M NaOH and stirred at room temperature for 4.5 hours, at 35°-40° C. for two hours, and at 65° C. for 15 hours. On cooling the solution was diluted with 3 mL of $CH_2Cl_2$ and neutralized to ~pH 7 with 1M HCl. The organic solvents were evaporated and the aqueous phase remaining was diluted with 20 mL of $CH_2Cl_2$, acidified, and separated. The aqueous layer was extracted with four 20 mL portions of $CH_2Cl_2$. The combined organic phases were washed with 20 mL of brine, dried over $MgSO_4$, and evaporated to obtain 229 mg (86%) of crude carboxylic acid as a clear oil.

TLC Silica gel (8:1:1 n$C_3H_7$OH: conc. $NH_3$:$H_2O$) $R_f$ 0.51.

$^1$H-NMR ($CDCl_3$) (270 Mz) δ 9.60 (br, 1H) 5.31 (t, 1H, J=6.0 Hz) 5.10 (m, 2H) 4.19 (m, 4H) 3.96 (d, 2H, J=6.0 Hz) 3.51 (m, 1H) 3.43 (m, 1H) 3.22 (ddd, 1H, J=23.1, 10.4, 3.3 Hz) 2.30-1.90 (m, 10H) 1.68 (s, 3H) 1.65 (s, 3H) 1.60 (s, 6H) 1.33 (t, 6H, J=7.0 Hz) ppm.

D.
(E,E)-2-(Dihydroxyphosphinyl)-4-[(3,7,11-trimethyl-2,6,10-dodecatrienyl)oxy]butanoic acid, trisodium salt To a solution of 227 mg (0.51 mmol) of Part C diester in 4 mL of $CH_2Cl_2$ at room temperature under argon was added 185 μL (1.40 mmol, 2.75 equiv) of 2,4,6-collidine and 370 μL (2.81 mmol, 5.5 equiv) of bromotrimethylsilane. After 15 hours, additional 34 μL (0.26 mmol, 0.5 equiv) of 2,4,6-collidine and 67 μL (0.51 mmol, 1 equiv) of bromotrimethylsilane were added. After two hours, the reaction mixture was evaporated. The residue was treated with 6.65 mL (6.65 mmol, 13 equiv) of 1M NaOH and lyophilized. Purification was by chromatography on an 8 cm height×2.5 cm diameter column of CHP-20P resin packed in water and eluted with 100 mL of $H_2O$ followed by a gradient created by the gradual addition of 300 mL of 1:1 $CH_3CN$:$H_2O$ into 300 mL of $H_2O$. Approximately 10 mL fractions were collected every 1.5 minutes. Fractions 31-42 were combined, evaporated, and lyophilized to provide 110.4 mg (48%) of title salt as a white lyophilate.

TLC Silica gel (5:4:1 n$C_3H_7$OH: con. $NH_3$:$H_2O$) $R_f$ 0.27.

IR (KBr) 3440 (br), 2967, 2925, 2873, 2857, 1696, 1635, 1568, 1438, 1386, 1167, 1085, 975, 484, 477, 471, 457, 449 cm$^{-1}$.

$^1$H-NMR ($D_2O$) (400 MHz) δ 5.36 (m, 1H) 5.17 (m, 2H) 4.03 (d, 2H, J=7.0 Hz) 3.49 (m, 1H) 3.41 (m, 1H) 2.50 (ddd, 1H, J=20.7, 11.7, 2.4 Hz) 2.20-1.90 (m, 10H) 1.67 (s, 6H) 1.60 (s, 3H) 1.59 (s, 3H) ppm.

$^{31}$P-NMR ($D_2O$) (36.2 MHz) δ 19.6 ppm.

($^{31}$P-NMR was accumulated in a proton-decoupled mode using 85% $H_3PO_4$ as an external reference.)

Mass Spec (FAB, +ions) m/e, 433 (M+2H-Na), 411 (M+3H-2Na).

Anal. calc'd for $C_{19}H_{30}O_6PNa_3$ + 1.02 $H_2O$: C, 48.27; H, 6.83; P, 6.55. Found: C, 47.97; H, 6.73; P, 6.44.

Karl Fischer analysis indicated 3.89% (1.02 mole) of water.

EXAMPLE 4

(E,E)-2-(Dihydroxyphosphinyl)-8,12,16-trimethyl-7,11,15-heptadecatrienoic acid, trisodium salt

A. Trishomofarnesyl iodide

A(1).
(E,E)-6,10,14-Trimethyl-5,9,13-pentadecatrienenitrile

A solution of 4.78 g (13.30 mmol) of (E,E)-14-iodo-2,6,10-trimethyl-2,6,10-tetradecatriene (prepared in Example 1 Part C) and 2.59 g (39.80 mmol) potassium cyanide in an 8:1 mixture of ethanol/water was stirred at reflux overnight. The ethanol was removed under vacuum and the reaction was diluted with 200 mL ether and 50 mL water. The aqueous fraction was removed and the organics washed with water and brine. The combined aqueous fractions were back extracted with ether and the combined organics dried o sodium sulfate and concentrated to yield 3.00 g (87%) of title nitrile as a yellow oil. The compound was used without further purification.

TLC (Silica gel, 95:5 hexane/ethyl acetate) $R_f=0.13$.
MS (CI - $NH_3$+ions) m/z 260 (M+H), 277 (M+$NH_4$).
IR (KBr) 2965, 2924, 2857, 2247, 1669, 1449, 1383, 1107, 833 cm$^{-1}$.
$^1$H NMR (CDCl$_3$, 400 MHz) δ 5.07 (m, 3H) 2.31 (t, 2H, J=7.5 Hz) 2.15 (q, 2H, J=7.5 Hz) 2.03 (m, 8H) 1.71 (quint, 2H, J=7.5 Hz) 1.67 (s, 3H) 1.63 (s, 3H) 1.60 (s, 6H) ppm.

A(2). (E,E)-6,10,14-Trimethyl-5,9,13-pentadecatrienal

To a stirred solution of 1.50 g (5.79 mmol) of Part A(1) nitrile in 6.0 mL tetrahrydrofuran at 0° C. was added dropwise 5.80 mL (8.69 mmol) of 1.5N diisobutylalumium hydride in toluene. After the addition was complete, the reaction was warmed to 50° C. in an oil bath for one hour. The the reaction was quenched at 0° C. with 6.0 mL water, and diluted with 26 mL 1M tartaric acid and 15 mL ether. The mixture stirred at room temperature for 2½ hours, and was extracted with ether two times. The combined organics were washed with brine, dried over sodium sulfate, and concentrated to provide 1.50 g of title aldehyde as a yellow slurry which was used without further purification.

TLC (Silica gel, CH$_2$Cl$_2$) $R_f=0.55$.
$^1$H NMR (CDCl$_3$, 400 MHz) δ 9.75 (s, 1H) 5.09 (m, 3H) 2.41 (dt, 2H, J=1.5, 7.3 Hz) 2.10–1.93 (m, 10H) 1.68 (s+m, 5H) 1.59 (s, 9H) ppm.

A(3).
(E,E)-6,10,14-Trimethyl-5,9,13-pentadecatrien-1-ol

To stirred solution of 1.50 g (5.77 mmol) of Part A(2) aldehyde in 15 mL methanol at 0° C. was added 330 mg (8.69 mmol) of sodium borohydride. After 15 minutes, the reaction was quenched with 5 mL ammonium chloride solution and partitioned between 100 mL ether and 50 mL ammonium chloride. The aqueous layer was removed and the organics were washed with brine, dried (sodium sulfate), and concentrated to 1.3 g of a yellow oil. The product was purified by flash chromatography on silica gel (150 g) packed, loaded, and eluted with 7:3 hexane/ethyl acetate. Pure fractions were concentrated to yield 0.80 g (45%) of title alcohol as a clear oil.

TLC (Silica gel 7:3 hexane/ethyl acetate) $R_f=0.32$.
MS (CI-NH$_3$, +ions) 265 (M+H), 282 (M+NH$_4$).
IR (CH$_2$Cl$_2$ film) 3331, 2928, 2859, 1451, 1383, 1061 cm$^{-1}$.
$^1$H NMR (CDCl$_3$, 400 MHz) δ 5.10 (m, 3H) 3.63 (t, 2H, J=6.5 Hz) 2.08 (m, 4H) 2.00 (m, 6H) 1.68 (s, 3H) 1.59 (s, 9H) 1.55 (m, 2H) 1.40 (quint, 2H, J=6.5 Hz) ppm.

A(4). Trishomofarnesyl iodide

To a stirred solution of 364 mg (1.38 mmol) of Part A(3) alcohol in 6 mL of dichloromethane at 0° C. was added 0.39 mL (2.76 mmol) of triethylamine followed by the dropwise addition of 0.14 mL (2.76 mmol) of methanesulfonyl chloride over 5 minutes. After stirring for 1 hour at 0° C., the mixture was diluted with ether and the organic phase was washed with 10% HCl, water, saturated NaCHO$_3$ and brine, dried (MgSO$_4$) and evaporated to give 459 mg of the mesylate as a colorless oil.

The crude mesylate was dissolved in 10 mL of acetone, treated with 414 mg (2.76 mmol) of sodium iodide and heated to 40° C. under argon for 17 hours. The mixture was diluted with hexane, washed with water, 4% sodium thiosulfate, water and brine, dried (MgSO$_4$), and evaporated to provide a colorless oil. Flash chromatography on 30 g of silica gel eluted with hexane gave 467 mg (90%) of the pure title iodide as a colorless oil.

TLC Silica gel (Hexane) $R_f=0.32$.
IR (CCl$_4$) 2965, 2927, 2854, 1449, 1381, 1222, 809 cm$^{-1}$.
$^1$H NMR(CDCl$_3$) (270 MHz): δ 5.10 (m, 3H) 3.18 (t, 2H, J=7 Hz) 2.00 (m, 10H) 1.82 (quint, 2H, J=7 Hz) 1.68 (s, 3H) 1.60 (s, 9H) 1.44 (m, 2H) ppm.
Mass Spec (CI-CH$_4$/N$_2$O, +ions) m/e 392 (M+NH$_4$), 375 (M+H).

B. (E,E)-2-(Diethoxyphosphinyl)-8,12,16-trimethyl-7,11,15-heptadecatrienoic acid, ethyl ester To a suspension of 228 mg (5.7 mmol, 3 equiv.) of a suspension of 60% sodium hydride in mineral oil washed three times with pentane, in 4 mL of tetrahydrofuran at room temperature under argon was added dropwise over five minutes 1.15 mL (5.7 mmol, equiv.) of triethyl phosphonoacetate. The mixture was allowed to stir for 0.5 hours, then treated with a solution of 711.3 mg (1.90 mmol) of Part A trishomofarnesyl iodide in 6 mL of tetrahydrofuran over fifteen minutes. After 45 hours the reaction mixture was diluted with 40 mL of diethylether and quenched with 3 mL of saturated NH$_4$Cl. The organic phase was washed with 5 mL of water and 5 mL of brine, dried over MgSO$_4$ and evaporated to give 1.04 g of crude product as a pale yellow oil. Purification by flash chromatography on 70 g of Merck 9385 silica, eluted with 3:7 ethyl acetate:hexanes provided 441.8 mg (50%) of title compound as a clear, colorless oil.

TLC Silica gel (1:1 ethyl acetate:hexanes) $R_f$0.21.
IR(CCl$_4$) 2980, 2928, 2856, 1735, 1443, 1368, 1256, 1162, 1097, 1054, 1028, 966, 813 cm$^{-1}$.
$^1$H-NMR (CDCl$_3$) (270 MHz): δ 5.02 (m, 3H) 4.20–4.00 (m, 6H) 2.85 (ddd, 1H, J=22.5, 11.1, 3.9 Hz) 2.10–1.70 (m, 12H) 1.60 (s, 3H) 1.52 (s, 9H) 1.25 (dt, 6H, J=1.65, 7.15 Hz) 1.21 (t, 3H, J=7.15 Hz) ppm.
Mass Spec (CI-NH$_3$, +ions) m/e 471 (M+H).

C.
(E,E)-2-(Diethoxyphosphinyl)-8,12,16-trimethyl-7,11,15-heotadecatrienoic acid A mixture of 435 mg (0.92 mmol) of Part B triester in 2.5 mL of ethanol, 1.5 mL of water and 1.00 mL (1.00 mmol, 1.09 equiv.) of 1M NaOH was stirred at room temperature for three hours, at 50° C. for 18 hours and at 80° C. for 24 hours. The reaction was cooled, diluted with 5 mL of $CH_2Cl_2$ and neutralized to pH 7 with 1M HCl. After evaporating the organic solvents, the aqueous residue was diluted with 20 mL of $CH_2Cl_2$, acidified with 1M HCl and extracted with four 20 mL portions of $CH_2Cl_2$. The combined organic phases were washed with 10 mL of brine, dried over $MgSO_4$ and evaporated to provide 405 mg ("100%") of title compound.

TLC silica gel (8:1:1 $nC_3H_7OH$:con. $NH_3$:$H_2O$) $R_f$ 0.70.

IR ($CCl_4$) 2980, 2969, 2929, 2858, 1736, 1443, 1393, 1384, 1378, 1257, 1221, 1165, 1098, 1053, 1026, 812, 807, 792, 779, 774, 751, $cm^{-1}$.

$^1$H-NMR ($CDCl_3$) (270 MHz): δ 10.12 (br, 1H) 5.10 (m, 3H) 4.20 (m, 4H) 2.96 (ddd, 1H, J=23.4, 10.9, 3.8 Hz) 2.10–1.90 (m, 10H) 1.68 (s, 3H) 1.60 (s, 6H) 1.58 (s, 3H) 1.75 (m, 2H) 1.33 (dt, 6H, J=7.0, 1.7 Hz) 1.50–1.20 (m, 4H) ppm.

Mass Spec ($CI-NH_3$, +ions) m/e 460 (M+$NH_4$), 443 (M+H), 399 (M+H - $CO_2$), 139.

D.
(E,E)-2-(Dihydroxyphosphinyl)-8,12,16-trimethyl-7,11,15-heptadecatrienoic acid, trisodium salt To a solution of 40.1 mg (0.90 mmol) of Part C compound and 330 μL (2.49 mmol, 2.75 equiv.) of 2,4,6-collidine in 8 mL of $CH_2Cl_2$ at room temperature under nitrogen was added dropwise over five minutes 650 μL (4.95 mmol, 5.5 equiv.) of bromotrimethylsilane, and the reaction was allowed to stir for 20 hours. The solvent was evaporated, and the residue was treated with 11.7 mL (11.7 mmol, 13 equiv.) of 1M NaOH and lyophilized. Purification was by chromatography on a 2.5 cm diameter×12 cm height column of HP-20 resin packed in water and eluted with 150 mL of water, followed by a gradient created by the gradual addition of 500 mL of 1:1 acetonitrile: water into 500 mL of water. Approximately 10 mL fractions were collected every 2 minutes. Fractions 39–60 were collected, evaporated, lyophilized to provide 320.0 mg (79%) of title salt as a flocculent, white lyophilate.

TLC silica gel (5:4:1 $nC_3H_7OH$:con. $NH_3$:$H_2O$) $R_f$ 0.25.

IR (KBr) 3426 (br), 2965, 2925, 2855, 1568, 1512, 1448, 1387, 1158, 1085, 975, 477, 470, 461 $cm^{-1}$.

$^1$H-NMR ($D_2O$) (400 MHz): δ 5.14 (t, 1H, J=6.8 Hz) 5.07 (t, 1H, J=7.7 Hz) 5.05 (t, 1H, J=7.7 Hz) 2.47 (ddd, 1H, J=17.4, 11.7, 3.0 Hz) 2.10–1.80 (m, 10H) 1.58 (s, 3H) 1.54 (s, 3H) 1.80–1.40 (m, 4H) 1.51 (s, 3H) 1.30–1.10 (m, 4H) ppm.

$^{31}$P-NMR ($D_2O$) (36.2 MHz): δ 21.5 ppm.

($^{31}$P-NMR was accumulated in a proton-decoupled mode with 85% $H_3PO_4$ as external reference).

Mass Spec (FAB, +ions) m/e 453 (M+H), 431 (M+2H-Na).

Anal. Calc'd for $C_{20}H_{32}O_5PNa_3$+1.07 $H_2O$: C, 50.93; H, 7.30; P, 6.57. Found: C, 50.91; H, 7.15; P, 6.88.

EXAMPLE 5
(E,E)-7,11,15-Trimethyl-2-phosphono-6,10,14-hexadecatrienoic acid, ethyl ester, disodium salt A solution of 456 mg (1.00 mmol) of Example 1 Part D triester in 4.0 mL of $CH_2Cl_2$ at ambient temperature was treated with 256 uL (2.00 mmol) of collidine and 0.42 mL (3.00 mmol) of TMSBr. The reaction mixture was stirred overnight and the volatiles were removed under reduced pressure. The residue was dissolved by the addition of 13 mL of 1M NaOH solution (13.0 mmol) and warming to 40° C. for 0.5 h. The solution was freeze dried and the crude solid was purified by MPLC on a column of CHP20P gel (2.5 diameter×13 cm height) eluted with water (200 mL) followed by a gradient created by the gradual addition of acetonitrile to a reservoir of 300 mL of water. The acetonitrile was removed under reduced pressure and the aqueous solution lyophilized to yield 250 mgs (50%) of the title disodium salt as a white lyophilate TLC: Silica gel (5:4:1 n-propanol/conc. $NH_3$/$H_2O$) $R_f$=0.79.

IR (KBr) 345, 3069, 2966, 2924, 2855, 1697, 1633, 1156, 1085, 977 $cm^{-1}$.

$^1$H NMR (270 MHz, $D_2O$) δ 5.10 (m,3H) 4.05 (m, 2H) 2.66 (dd, 1H,J=18.2, 12.3 Hz) 2.20–1.80 (m, 12H) 1.57 (s, 3H) 1.52 (s,3H), 1.47 (s+m,8H), 1.19 (t, 3H, J=7.1 Hz) ppm.

Anal. Calcd. for: $C_{21}H_{35}PO_5Na_2$+0.86 $H_2O$: C, 54.85; H, 8.05; P, 6.74. Found: C, 54.83; H, 8.13; P, 6.97.

Mass Spec (FAB, +ions) m/e 445 (M+H), 423 (M-Na+2H).

EXAMPLE 6
(E,E)-7,11,15-Trimethyl-2-phosphono-6,10,14-hexadecatrienoic acid. 3-phenylpropyl ester, disodium salt

A.
(E,E)-2-(Diethoxyphosphinyl)-7,11,15-trimethyl-6,10,14-hexadecatrienoic acid To a stirred solution of 500 mg (1.10 mmol) of Example 1 Part D compound in 5 mL of ethanol at RT under argon was added 1.65 mL (1.65 mmol) of 1N NaOH in 3.35 mL water. The mixture was heated to 55° C. and stirred for 18 h at which time it was acidified with 50 mL of 1:1 $KHSO_4$:$H_2O$ and extracted with EtOAc. The organic layer was dried over $MgSO_4$ and the solvent evaporated to provide 443 mg of a pale yellow oil. Flash chromatography was performed on 40 g silica gel, packed, loaded and eluted with 95:5 $CH_2Cl_2$:MeOH (1 liter), then eluted with 90:10 $CH_2Cl_2$: MeOH plus 1% acetic acid (1 liter). Pure product fractions were combined and evaporated to provide 413 mg (88%) of title compound as a pale yellow oil.

TLC Silica gel (8:1:1 n-propanol:conc. $NH_3$:$H_2O$) $R_f$=0.64.

$^1$H-NMR (270 MHz, $CDCl_3$): δ 5.10 (m, 3H) 4.13 (m, 4H) 2.80 (ddd, 1H, J=3.7, 10.7, 21.7 Hz) 2.07–1.95 (m, 11H) 1.66 (s, 3H) 1.61 (s. 6H) 1.58 (s, 6H) 1.50–1.90 (m, 2H) 1.42–1.37 (m, 1H) 1.1 (t, 6H, J=7.04 Hz) ppm.

B.
(E,E)-2-(Diethoxyphosphinyl)-7,11,15-trimethyl-6,10,14-hexadecatrienoic acid, 3-phenvlpropyl ester To a stirred solution of 413 mg (0.96 mmol) of Part A compound in 4 mL dry DMF at RT under argon was added 200 mg (1.45 mmol) of $K_2CO_3$ and 420 mg (1.45 mmol) of 3-phenylpropyl toluene-4-sulfonate. The mixture stirred at RT for 18 h, at which time it was diluted with 200 mL of 1:1 EtOAc:H$_2$O. The organic layer was washed with water, brine and dried over MgSO$_4$. The solvent was evaporated to provide 625 mg of a pale yellow oil. Flash chromatography was performed on 40 g of silica gel, packed, loaded and eluted with 70:30 Hexane:EtOAc. Pure product fractions were combined and evaporated to provide 400 mg (76%) of title compound as a pale yellow oil.

TLC Silica gel (49.5:49.5:1 Hexane/EtOAc/Acetic Acid) R$_f$=0.44.

$^1$H-NMR (270 MHz, CDCl$_3$): δ 7.20 (m, 5H) 5.10 (m, 3H) 4.15 (m, 6H) 3.00 (ddd, 1H, J=4.11, 10.85, 22.56 Hz) 2.78 (t, 2H, J=7.62 Hz) 2.10–1.80 (m, 14H) 1.67 (s, 3H) 1.59 (s, 6H) 1.57 (s, 3H) 1.40 (m, 2H) 1.30 (t, 3H, J=6.45 Hz) ppm.

C.

(E,E)-7,11,15-Trimethyl-2-phosphono-6,10,14-hexadecatrienoic acid, 3-phenylpropyl ester disodium salt To a stirred solution of 455 mg (0.83 mmol) of Part B compound in 4 mL of CH$_2$Cl$_2$ at RT under argon was added 225 μL (1.7 mmol) of 2,4,6-collidine followed by 330 μL (2.5 mmol) of bromotrimethylsilane. The mixture stirred for 18 h at RT at which time the solvent was evaporated and pumped on at high vacuum for 20 min. The remainder was dissolved in 4 mL (4.0 mmol) of 1N NaOH and warmed to 40° C. for 0.5 h then lyophilized. The crude material was purified by MPLC on a column of CHP20P (2.5 cm diameter×18 cm height) eluted with water (fractions 1 to 10 (15 mL) followed by a gradient created by the gradual addition of 300 mL of 60:40 CH$_3$CN:H$_2$O to a reservoir of 300 mL H$_2$O. Pure product fractions were combined and evaporated to remove CH$_3$CN then lyophilized to provide 374 mg (92%) of title compound as a white lyophilate.

TLC Silica gel (5:4:1 n-propanol:conc. NH$_3$:H$_2$O) R$_f$=0.61.

IR (Ksr) 3452, 3436, 3433, 3426, 3413, 3272, 2962, 2924, 2855, 1697, 1452, 1340, 1156, 1112, 982, 698 cm$^{-1}$.

Mass Spec (FAB, +ions) m/e 557 (M+Na), 535 (M+H), 513 (M+2H-Na).

Anal. calc'd for C$_{28}$H$_{41}$PO$_5$Na$_2$+1.25 H$_2$O: C, 60.38; H, 7.87; P, 5.56. Found C, 60.48; H, 7.91; P, 5.67.

$^1$H-NMR (400 MHz, D$_2$O): δ 7.20 (m, 5H) 5.13 (m, 1H) 5.07 (m, 2H) 4.00–4.20 (m, 2H) 2.65–2.80 (m, 1H) 2.70 (t, 2H, J=7.92) 2.10–1.82 (m, 14H) 1.64 (s, 3H) 1.56 (s, 6H) 1.35–1.24 (m, 2H) ppm.

EXAMPLE 7

(E,E)-2-Chloro-7,11,15-trimethyl-2-phosphono-6,10,14-hexadecatrienoic acid, trisodium salt

A.

(E,E)-2-Chloro-2-(diethoxyphosphinyl)-7,11,15-trimethyl-6,10,14-hexadecatrienoic acid, ethyl ester To a stirred solution of 0.61 g (1.33 mmol) of Example 1 Part D triester in 5 mL of THF at 0° C. was added 1.59 mL (1.59 mmol) of 1M sodium bis(trimethylsilyl)amide in THF over 2 min. to give a light yellow solution. After 30 min. 0.21 g (1.59 mmol) of N-chlorosuccinimide (NCS) was added quickly to the reaction mixture. The reaction was allowed to stir for 0.2 h at RT when it was quenched with saturated NH$_4$Cl solution and diluted with ethyl acetate. The resulting biphasic mixture was equilibrated and the organic fraction separated. The aqueous layer was re-extracted with ethyl acetate and the organic fractions combined, dried (MgSO$_4$) and concentrated to give a yellow oil. Flash chromatography was preformed on 50 g of silica gel packed, loaded and eluted with 4:6 ethyl acetate:hexane to provide 0.59 g (90%) of title compound as a lightly colored oil.

TLC Silica gel (6:4 ethyl acetate: hexane) R$_f$=0.66.

$^1$H NMR (CDCl$_3$, 270 MHz) δ 5.10 (t, 3H, J=5.5 Hz) 4.30 (m, 6H) 2.45 (m, 1H)
2.10 ∝ 1.90 (m, 11H)
1.70–1.50 (m, 2H)
1.70 (s, 3H)
1.63 (s, 9H)
1.30–1.10 (m, 9H) ppm.

B.

(E,E)-2-Chloro-2-(diethoxyphosphinyl)-7,11,15-trimethyl-6,10,14-hexadecatrienoic acid To a stirred solution of 0.59 g (1.20 mmol) of Part A triester in 4 mL of ethanol was added 2.5 mL (2.5 mmol) of a 1M sodium hydroxide solution. The reaction flask was heated to 75° C. (bath temp.) for 5 h, at which point the reaction was diluted with 5% KHSO$_4$ solution. The acidic mixture was extracted with ethyl acetate, dried (MgSO4), and concentrated to provide the crude acid. Flash chromatography was performed on 25 g of silica gel packed, loaded and eluted with 95:5:0.2 methylene chloride: methanol: acetic acid to provide 0.32 g (58%) of title compound as an amber oil.

TLC Silica gel (1:9 methanol:methylene chloride) R$_f$=0.33.

$^1$H NMR (CDCl$_3$, 270 MHz) δ 10.70 (s, 1H) 5.03 (s, 3H) 4.10 (m, 4H)
2.35 (m, 1H) 2.10–1.90 (m, 11H) 1.55 (m, 1H) 1.60 (s, 3H) 1.52 (s, 9H) 1.25–1.10 (m, 7H) ppm.

C.

(E,E)-2-Chloro-7,11,15-trimethyl-2-phosphono-6,10,14-hexadecatrienoic acid, trisodium salt To a stirred solution of 0.32 g (0.69 mmol) of Part B compound in 6.0 mL of methylene chloride under argon at RT was added 0.27 mL (2.07 mmol) of 2,4,6-collidine followed by 0.32 mL (2.40 mmol) of bromotrimethylsilane and the reaction was stirred for 18 h. The solvent was removed under reduced pressure (15 mm Hg) and pumped (1 mm Hg) for 1 h. The semisolid residue was dissolved in 8 mL (4 mmol) of 0.5 M NaOH solution, stirred for 1 h, diluted with 10 mL of water and lyophilized. The crude solids were purified by MPLC on a column of CHP20P gel (2.5 diameter×10 cm height) eluting with water (120 mL) followed by a gradient created by the gradual addition of acetonitrile to a reservoir of 300 mL of water. The acetonitrile was removed under reduced pressure and the aqueous solution lyophilized to provide 0.18 g (64%) of title salt as a white lyophilate.

TLC Silica gel (5:4:1 n-propanol:conc. NH$_3$:water) R$_f$=0.41.

IR (KBr) 3436, 3276, 2925, 2856, 1601, 1449, 1437, 1374, 1099, 981 cm$^{-1}$.

$^1$H NMR (D$_2$O, 400 MHz) δ 5.18 (t, 1H, J=7.0 Hz) 5.12 (q, 2H, J=6.6 Hz) 2.40 (m, 1H) 2.10–1.80 (m, 11H) 1.62 (s, 3H) 1.55 (s, 9H) 1.54 (m, 1H) 1.24 (m, 1H) ppm.

Mass Spec (FAB, + ions) m/e 496 (M+Na), 473 (M+H), 451 (M-Na+2H), 428 (M-2Na+3H).

Anal. calc'd for $C_{19}H_{29}O_5ClPNa_3 + 1.40\ H_2O$: C, 45.82; H, 6.44; P, 6.22; Cl, 7.12. Found: C, 45.77: H, 6.74: P, 6.21; Cl, 7.42.

EXAMPLE 8

(E,E)-2,7,11,15-Tetramethyl-2-phosphono-6,10,14-hexadecatrienoic acid, disodium salt

A.

(E,E)-2-(Diethoxyphosphinyl)-2,7,11,15-tetramethyl-6,10,14-hexadecatrienoic acid, ethyl ester To a stirred solution of 0.61 g (1.33 mmol) of Example 1 Part D triester in 5 mL of THF at 0° C. was added 1.59 mL (1.59 mmol) of 1M sodium bis(trimethylsilyl)amide in THF over 2 min. to give a light yellow solution. After 30 min. 116 uL (0.26 g, 1.86 mmol) of methyl iodide was added quickly to the reaction mixture. The reaction was allowed to stir for 1 h at RT when it was quenched with saturated $NH_4Cl$ solution and diluted with ethyl acetate. The resulting biphasic mixture was equilibrated and the organic fraction separated. The aqueous layer was re-extracted with ethyl acetate and the organic fractions combined, dried ($MgSO_4$) and concentrated to give a yellow oil. Flash chromatography was preformed on 125 g of silica gel packed, loaded and eluted with 1:1 ethyl acetate:hexane to provide 0.58 g (93%) of title compound as a lightly colored oil.

TLC Silica gel (6:4 ethyl acetate: hexane) $R_f = 0.40$.

$^1$H NMR ($CDCl_3$, 270 MHz) δ 5.03 (t, 3H, J=6.0 Hz) 4.10 (m, 6H) 2.10–1.90 (m, 12H) 1.70–1.50 (m, 2H) 1.60 (s, 3H) 1.51 (s, 9H) 1.34 (d, 3H, J=17.1 Hz) 1.25–1.10 (m, 11H) ppm.

B.

(E,E)-2-(Diethoxyphosphinyl)-2,7,11,15-tetramethyl-6,10,14-hexadecatrienoic acid To a stirred solution of 0.58 g (1.23 mmol) of Part A triester in 4 mL of ethanol was added 5 mL (5 mmol) of a 1M sodium hydroxide solution. The reaction flask was heated to 75° C. (bath temp.) for 75 h, at which point the reaction was diluted with 5% $KHSO_4$ solution. The acidic mixture was extracted with ethyl acetate, dried ($MgSO4$), and concentrated to provide 0.51 g (94%) of title compound as a thick oil.

TLC Silica gel (1:9 methanol:methylene chloride) $R_f = 0.40$.

$^1$H NMR ($CDCl_3$, 270 MHz) δ 9.00 (s, 1H) 5.03 (t, 3H, J=6.4 Hz) 4.10 (sept., 4H, J=7.0 Hz) 2.10–1.90 (m, 11H) 1.55 (m, 1H) 1.60 (s, 3H) 1.52 (s, 9H) 1.34 (d, 3H, J=17.1 Hz) 1.25–1.10 (m, 8H) ppm.

C.

(E,E)-2,7,11,15-Tetramethyl-2-phosphono-6,10,14-hexadecatrienoic acid, disodium salt To a stirred solution of 0.50 g (1.13 mmol) of Part B compound in 5.0 mL of methylene chloride under argon at RT was added 0.45 mL (3.39 mmol) of 2,4,6-collidine followed by 0.59 mL (4.40 mmol) of bromotrimethylsilane and the reaction was stirred for 18 h. The solvent was removed under reduced pressure (15 mm Hg) and pumped (1 mm Hg) for 1 h. The semisolid residue was dissolved in 15 mL (5 mmol) of 0.3M NaOH solution, stirred for 1 h, diluted with 10 mL of water and lyophilized. The crude solids were purified by MPLC on a column of CHP20P gel (2.5 diameter × 18 cm height) eluted with water (250 mL) followed by a gradient created by the gradual addition of acetonitrile to a reservoir of 400 mL of water. The acetonitrile was removed under reduced pressure and the aqueous solution lyophilized to provide 0.37 g (72%) of title salt as a white lyophilate.

TLC Silica gel (5:4:1 n-propanol:conc. $NH_3$:water) $R_f = 0.41$.

IR (KBr) 3430, 3051, 2965, 2957, 1639, 1562, 1387, 1359, 1157, 1068, 891 cm$^{-1}$.

$^1$H NMR ($D_2O$, 400 MHz) δ 5.18 (t, 1H, J=7.0 Hz) 5.12 (m, 2H) 2.10–1.90 (m, 11H) 1.60 (s, 3H) 1.55 (s, 9H) 1.54 (m, 1H) 1.34 (m, 1H) 1.18 (d, 3H, J=15.0 Hz) 1.10 (m, 1H) ppm.

Mass Spec (FAB, + ions) m/e 453 (M+Na), 431 (M+H), 409 (M-Na+H).

Anal. calc'd for $C_{20}H_{33}O_5Na_2P + 1.0\ H_2O$: C, 53.57; H, 7.87; P, 6.91. Found: C, 53.55: H, 7.98: P, 7.30.

EXAMPLE 9

(E,E)-2-Hydroxy-7,11,15-trimethyl-2-phosphono-6,10,14-hexadecatrienoic acid, trisodium salt

A.

(E,E)-2-(Benzoyloxy)-2-(diethoxyphosphinyl)-7,11,15-trimethyl-6,10,14-hexadecatrienoic acid, ethyl ester To a stirred solution of 0.46 g (1.01 mmol) of Example 1 Part D triester in 5 mL of THF at 0° C. was added 1.06 mL (1.06 mmol) of 1M sodium bis(trimethylsilyl)amide in THF over 2 min. to give a light yellow solution. After 30 min. 0.27 g (1.10 mmol) of dibenzoyl peroxide was added in one portion to the reaction mixture. The reaction was allowed to stir for 1 h at RT when it was quenched with saturated $NH_4Cl$ solution and diluted with ether. The resulting biphasic mixture was equilibrated and the organic fraction separated. The aqueous layer was re-extracted with ether and the organic fractions combined, dried ($MgSO_4$) and concentrated to give a yellow oil. Flash chromatography was preformed on 50 g of silica gel packed, loaded and eluted with 1:1 ethyl acetate:hexane to provide 0.54 g (93%) of title compound as a lightly colored oil.

TLC Silica gel (6:4 ethyl acetate:hexane) $R_f = 0.66$.

$^1$H NMR ($CDCl_3$, 270 MHz) δ 7.97 (d, 2H, J=5.9 Hz) 7.47 (t, 1H, J=6.4 Hz) 7.35 (t, 2H, J=7.6 Hz) 5.03 (s, 3H) 4.10 (m, 6H) 2.40 (m, 2H) 2.10–1.90 (m, 11H) 1.75 (m, 1H) 1.56 (s, 3H) 1.48 (s, 9H) 1.25–1.10 (m, 9H) ppm.

B (E,E)-2-Hydroxy-7,11,15-trimethyl-2-phosphono-6,10,14-hexadecatrienoic acid, trisodium salt To a stirred solution of 0.35 g (0.60 mmol) of Part A compound in 4.0 mL of methylene chloride under argon at RT was added 0.24 mL (1.80 mmol) of 2,4,6-collidine followed by 0.33 mL (2.40 mmol) of bromotrimethylsilane and the reaction was stirred for 18 h. The solvent was removed under reduced pressure (15 mm Hg) and pumped (1 mm Hg) for 1 h. The semisolid residue was dissolved in 15.0 mL (7.5 mmol) of 0.5M NaOH solution, stirred for 24 h at 80 ° C. (bath temperature), diluted with 5 mL of water and lyophilized. The crude solids were purified by MPLC on a column of CHP20P gel (2.5 diameter × 8 cm height) eluted with water (200 mL) followed by a gradient created by the gradual addition of acetonitrile to a reservoir of 300 mL of water. The acetonitrile was removed under reduced pressure and the aqueous solution lyophilized to provide 0.13 g (45%) of title salt as a white lyophilate.

TLC Silica gel (5:4:1 n-propanol:conc. $NH_3$:water) $R_f = 0.31$.

IR (KBr) 3420, 2965, 2925, 2857, 1600, 1437, 1385, 1099 cm$^{-1}$.

$^1$H NMR (D$_2$O, 400 MHz) δ 5.20 (t, 1H, J=7.0 Hz) 5.12 (q, 2H, J=6.0 Hz) 2.10–1.90 (m, 10H) 1.65 (m, 2H) 1.63 (s, 3H) 1.56 (s, 9H) 1.34 (m, 1H) 1.10 (m, 1H) ppm.

Mass Spec (FAB, + ions) m/e 478 (M+Na), 455 (M+H), 433 (M-Na+2H), 411 (M-2Na+3H).

Anal. calc'd for C$_{19}$H$_{30}$O$_6$Na$_3$P+1.15 H$_2$O: C, 48.Q4; H, 6.85; P, 6.52. Found: C, 48.32: H, 7.17: P, 6.45.

EXAMPLE 10

(E,E)-2-Hydroxymethyl-7,11,15-trimethyl-2-phosphono-6,10,14-hexadecatrienoic acid, trisodium salt

A.

(E,E)-2-(Diethoxyphosphinyl)-7,11,15-trimethyl-6,10,14-hexadecatrienoic acid, t-butyl ester To a stirred solution of 400 mg (16.66 mmol) of NaH in 30 mL of dry THF at 0° C. under argon was added 4.18 g (16.60 mmol) of t-butyldiethyl phosphonoacetate over 20 min. The mixture stirred for 0.5 h at 0° C. when 2.00 g (5.60 mmol) of Example 1 Part C iodide was added dropwise. After 18 h at room temperature, the reaction was quenched with saturated NH$_4$Cl and diluted with ether. The organic layer was washed with water, brine, dried over MgSO$_4$ and evaporated to provide 3.60 g of a crude pale yellow oil. Flash chromatography was performed on 100 g of silica gel eluted with 60:40 hexane/EtOAc. Pure product fractions were combined and evaporated to provide 1.81 g (67%) of title compound as a clear pale yellow oil.

TLC Silica gel (1:1 hexane/EtOAc) R$_f$=0.48

IR (CCl$_4$): 2980, 2930, 2858, 1730, 1253, 1055, 1028, 966.

$^1$H NMR (270 MHz, CDCl$_3$) δ 5.10 (t, 3H, J=6.45) 4.14 (m, 4H) 2.83 (ddd, 1H, J=4.1, 11.1, 22.3 Hz) 1.97 (m, 10H) 1.80–1.20 (m, 4H) 1.61 (s, 3H) 1.59 (s, 9H) 1.55 (s, 9H) 1.32 (td, 6H, J=7.04, 2.00 Hz) ppm.

Mass Spec (CI-NH$_3$, + ions) 502 (M+NH$_4$), 485 (M+H), 429 (M+H-t-Butyl)

B. Iodomethyl pivalate

To a stirred solution of 8.00 g (53.30 mmol) of chloromethyl pivalate in 100 mL of acetone at RT under argon was added 24.00 g (160.00 mmol) of NaI. The mixture was heated to 40° C. for 4 h at which time the solids were removed by filtration and the filtrate was evaporated. The residue was diluted with ether, washed sequentially with water, 5% Na$_2$S$_2$O$_7$, brine, and dried over MgSO$_4$. Evaporation of the solvent provided 9.60 g (75%) of title compound as a light green oil.

$^1$H NMR (270 MHz, CDCl$_3$) δ 5.98 (s, 2H; 1.10 (s, 9H) ppm.

(E,E)-2-(Diethoxyphosphinyl)-2-[(2,2-dimethyl-1-oxopropoxy)methyl]-7,11,15-trimethyl-6,10,14-hexadecatrienoic acid, 1,1-dimethylethyl ester To a stirred solution of 48.0 mg (2.00 mmol) of NaH in 15 mL of dry THF at 0° C. under argon was added 800 mg (1.65 mmol) of Part A compound over 10 min. The mixture was stirred for 0.5 h at 0° C. when 440 mg (1.82 mmol) of iodomethyl pivalate was added dropwise over 10 min. The mixture stirred for 1.5 h at 0° C. and was quenched by the addition of saturated NH$_4$Cl and ether. The organic layer was washed with water, brine, dried over MgSO$_4$ and the solvent evaporated to provide 942 mg of a crude yellow oil. Flash chromatography was performed on 100 g of silica gel eluted with 60:40 hexane/EtOAc. Pure product fractions were combined and evaporated to provide 750 mg (76%) of title compound as a yellow oil.

TLC Silica gel (1:1 hexane:EtOAc) R$_f$=0.63

IR (CCl$_4$) 2926, 2854, 1734, 1465, 1149.

$^1$H NMR (270 MHz, CDCl$_3$) δ 5.20 (m, 3H) 4.52 (d, 2H, J=12.9 Hz) 4.24 (m, 4H) 2.10 (m, 12H) 1.76 (s, 3H) 1.69 (s, 9H) 1.56 (s, 9H) 1.41 (t, 6H, J=7.04 Hz) 1.30 (s, 9H) 1.32–1.65 (m, 2H) ppm.

Mass Spec (CI-NH$_3$, + ions) 616 (M+NH$_4$), 599 (M+H).

D.

(E,E)-2-Hydroxymethyl-7,11,15-trimethyl-2-phosphono-6,10,14-hexadecatrienoic acid, trisodium salt {To a stirred solution of 700 mg (1.17 mmol) of Part C compound in 15 mL of CH$_2$Cl$_2$ under argon at 0° C. was added 0.618 mL (4.68 mmol) of 2,4,6-collidine followed by 0.92 mL (6.43 mmol) of iodotrimethylsilane. The reaction was brought to RT then heated to 50° C. for 66 h at which time an additional 0.080 mL (0.56 mmol) of iodotrimethylsilane was added. The reaction was stirred at 50° C. for 18 h, when the solvent was evaporated and pumped on at high vacuum for 20 min. The remainder was dissolved in 17 mL (8.50 mmol) of 0.5M sodium hydroxide solution, heated to 80° C. for 42 h and lyophilized. The crude lyophilate was purified by MPLC on a column of CHP20P gel (2.5 cm diameter×25 cm height) eluted with water (fractions 1 to 10) followed by a gradient created by the gradual addition of 400 mL of 30:70 water/CH$_3$CN to a reservoir of 400 mL of water. Approximately 15 mL fractions were collected. Pure product fractions were combined and evaporated to remove CH$_3$CN and then lyophilized to provide 150 mg (27%) of title salt as a white lyophilate.

TLC Silica gel (5:4:1 n-propanol/conc. NH$_3$/H$_2$O) R$_f$=0.25.

IR (KBr) 3445, 3429, 3273, 3246, 2962, 2924, 2856, 1633, 1566, 1448, 1383, 1163, 1089, 964, 877, 605 cm$^{-1}$.

$^1$H NMR (D$_2$O, 400 MHz) δ 5.20 (t, 1H, J=6.78 Hz) 5.15 (q, 2H, J=6.78 Hz) 3.86 (t, 1H J=11.36 Hz) 3.69 (dd, 1H, J=11.36, 22.35 Hz) 2.05, 1.95 (two m, 10H) 1.87, 1.65 (two m, 2H) 1.60 (s, 3H) 1 55 (s, 9H) 1.30, 1.13 (two m, 2H) ppm.

Mass Spec (FAB, +ions) m/e 469 (M+H), 447 (M-Na+2H), 425 (M-2Na+3H).

Anal. calc'd for C$_{20}$H$_{32}$O$_6$PNa$_3$+0.70 H$_2$O: C, 49.94; H, 7.00; P, 6.44. Found C, 50.24; H, 7.39; P, 6.62.

EXAMPLE 11

(E,E)-2-Fluoro-7,11,15-trimethyl-2-phosphono-6,10,14-hexadecatrienoic acid, trisodium salt

A. (Diethoxyphosphinyl)fluoroacetic acid, ethyl ester

A mixture of 4.00 g (24.0 mmol) of triethyl phosphite and 4.45 g (24.0 mmol) of ethyl bromofluoroacetate (purchased from PCR Inc. Gainesville, Fla.) was heated to 150° C. for 4 h under argon. The contents of the flask were cooled to RT and then distilled under vacuum (0.5 mm Hg) to provide 4.5 g (77%) of title compound as a colorless oil.

Bp. 100° C./0.5 mm.

$^1$H NMR (270 MHz, CDCl$_3$) δ 5.18 (dd, 1H, J=46.9, 12.3 Hz) 4.30 (q, 2H, J=7.0 Hz) 4.20 (m, 4H) 1.30 (m, 9H) ppm.

B.

(E,E)-2-(Diethoxyphosphinyl)-2-fluoro-7,11,15-trimethyl-6,10,14-hexadecatrienoic acid, ethyl ester To a stirred solution of 0.12 g (5.00 mmol) of NaH in a 1:1 mixture of DMF:THF at 0° C. was added 1.21 g (5.00 mmol) of Part A compound dropwise over 0.2 h. After 0.5 h at 0° C. the yellow solution was treated with Example 1 Part C iodide in one portion and allowed to warm to RT. After 5 h at RT the reaction was quenched with by the addition of brine and partitioned between ethyl acetate and water. The organics were dried over $Na_2SO_4$ and evaporated to provide a crude yellow oil. Flash chromatography was performed on 100 g of silica gel packed and loaded with 3:7 ethyl acetate:hexanes and eluted with 1:1 ethyl acetate:hexanes to give 1.43 g (60%) of title compound as a lightly colored oil.

TLC Silica gel (2:1 ethyl acetate:hexane) $R_f=0.66$.
IR (KBr) 2980, 2928, 1759, 1738, 1267, 1022 $cm^{-1}$.
$^1H$ NMR (270 MHz, $CDCl_3$) δ 5.00 (m, 3H) 4.20 (m, 6H) 2.30–1.80 (m, 12H) 1.59 (s, 3H) 1.55 (m, 1H) 1.51 (s, 9H) 1.27 (m, 9H) 1.20 (m, 1H) ppm.

Mass Spec (CI, $NH_3$, +ions) m/e 475 (M+H), 492 (M+$NH_4$).

C.

(E,E)-2-(Diethoxyphosphinyl)-2-fluoro-7,11,15-trimethyl-6,10,14-hexadecatrienoic acid A stirred solution of 1.35 g (3.00 mmol) of Part B triester in 6 mL of ethanol was treated with 6.0 mL (6.00 mmol) of 1M NaOH solution. The reaction mixture was stirred for 5 h at RT and quenched with 5% $KHSO_4$ solution. The acidic mixture was extracted with ethyl acetate, dried over $Na_2SO_4$ and evaporated to provide 1.27 g (95%) of the title acid as a thick oil.

TLC Silica gel (2:1 ethyl acetate:hexane) $R_f=0.10$.
IR (KBr) 3600–2400 (broad), 2968, 2924, 2858, 1757, 1442, 1224, 1165, 1024 $cm^{-1}$.
$^1H$ NMR (270 MHz, $CDCl_3$) δ 10.50 (s,1H) 5.00 (m, 3H) 4.25 (m, 4H) 2.30–1.80 (m, 12H) 1.60 (m, 3H) 1.55 (m, 1H) 1.52 (s, 9H) 1.27 (m, 6H) 1.20 (m, 1H) ppm.

Mass Spec (CI, $NH_3$, +ions) m/e 447 (M+H), 464 (M+$NH_4$).

D.

(E,E)-2-Fluoro-7,11,15-trimethyl-2-phosphono-6,10,14-hexadecatrienoic acid, trisodium salt To a stirred solution of 1.27 g (2.85 mmol) of Part C acid in 10 mL of dichloromethane under argon at 0° C. was added 1.26 mL (9.50 mmol) of 2,4,6-collidine followed by 1.86 mL (14.00 mmol) of bromotrimethylsilane. The reaction was allowed to stir for 18 h at RT when the solvent was evaporated under reduced pressure and the semisolid residue pumped under high vacuum for 1 h. The remaining residue was dissolved in 30 mL (15.00 mmol) of 0.5M NaOH solution, diluted to a volume of 45 mL with water and lyophilized. The crude lyophilate was purified by MPLC in a column of CHP20P (2.5 cm diameter×20 cm height) eluted with water (300 mL) followed by a gradient created by the gradual addition of acetonitrile to a reservoir of 400 mL of water. Approximately 12 mL fractions were collected. The acetonitrile was evaporated at reduced pressure and the aqueous solution was lyophilized to provide 0.75 g (65%) of title salt as a white lyophilate.

TLC Silica gel (5:4:1 n-propanol:con. $NH_3$:$H_2O$) $R_f=0.42$.

IR (KBr) 3445, 2964, 2924, 2856, 1602, 1390, 1128, 987 $cm^{-1}$.
$^1H$ NMR (400 MHz, $D_2O$) δ 5.21 (t, 1H, J=6.7 Hz) 5.15 (q, 2H, J=7.0 Hz) 2.20–1.80 (m,12H) 1.62 (s, 3H) 1.55 (s, 9H) 1.40 (m, 1H) 1.15 (m, 1H) ppm.
$^{19}F$ NMR ($D_2O$) δ −170.6 (ddd, J=74.5, 37.5, 10 Hz) ppm.
$^{31}P$ NMR ($D_2O$) δ 11.89 (d, J=74.7 Hz) ppm.

Mass Spec (FAB, +ions) 479 (M+Na), 457 (M+H), 435 (M+2H-Na).

Anal. Calc'd for $C_{19}H_{29}FO_5PNa_3+0.75$ $H_2O$: C, 48.52; H, 6.55; P, 6.79; F, 4.04. Found: C, 48.52; H, 6.84; P, 6.59; F, 4.27.

EXAMPLE 12

(E,E)-6,10,14-Trimethyl-2-phosphono-5,9,13-pentadecatrienoic acid, trisodium salt (SQ34,738)

A. (E,E)-4,8,12-Trimethyl-3,7,11-tridecatrien-1-ol (1) (E,E)-3,7,11-Trimethyl-2,6,10-dodecatrienaldehyde [(E,E)-Farnesal]

A solution of oxalyl chloride (4.68 g, 0.037 mol) in dry $CH_2Cl_2$ under argon atmosphere was cooled to −65° C. A solution of 5.33 mL of dimethyl sulfoxide (DMSO) (0.68 mol) in $CH_2Cl_2$ (17 mL) was added rapidly, dropwise, to the cooled oxalyl chloride solution. After stirring for 7 minutes at −65° C., a 10 mL $CH_2Cl_2$ solution of (E,E)-farnesol (7.0 g, 0.032 mol) was added over 10 minutes to the reaction solution at −65° C.: a precipitate formed upon the addition of approximately half of the farnesol solution. After the addition of the farnesol solution was completed, the reaction was stirred at −65° C. for 25 minutes, and then 22.4 mL (0.16 mol) of triethylamine was added over 10 minutes. After stirring for an additional 15 minutes at −65° C., the reaction was warmed to room temperature, and then diluted with water (~200 mL). The resulting aqueous layer was extracted several times with $CH_2Cl_2$. The combined organic layers were washed once with saturated aqueous NaCl solution, once with 1% HCl, once with 5% $Na_2CO_3$ solution and once with saturated aqueous NaCl solution. The resulting organic layer was dried over $MgSO_4$ to give 7.05 g (100%) of a clear oil after filtration and solvent removal.

TLC Silica gel (20% ethyl acetate/hexane) $R_f=0.34$.
$^1H$ NMR ($CDCl_3$, 270 MHz): δ 9.98 (d, 1H, J=7 Hz), 5.88 (broad d, 1H, J=7 Hz), 5.08 (m, 2H), 2.22 (m, 4H), 2.17 (s, 3H), 2.02 (m, 4H), 1.66 (s, 3H), 1.60 (s, 6H) ppm.
$^{13}C$-NMR ($CDCl_3$) (67.8 MHz) δ 191.0, 163.6, 136.5, 131.3, 127.4, 124.0, 122.4, 40.5, 39.6, 26.6, 25.6, 17.6, 17.5, 15.9 ppm.

(2) 4,8,12-Trimethyl-1,3,7,11-tridecatetraene

A suspension of methyltriphenylphosphonium iodide (8.07 g, 0.02 mole) in 61 mL of dry tetrahydrofuran (THF), under argon atmosphere was cooled to 0° C. To this suspension at 0° C. was added 9 mL (18 mmol) of phenyllithium (2.0M in diethyl ether/hexane 30:70) over 10 minutes. After the addition was complete, the reaction mixture containing excess phosphonium salt was warmed to room temperature and stirred for 40 minutes. The reaction mixture was then recooled to 0° C., and a 10 mL THF solution of the Part (1) aldehyde (4.0 g, 0.018 mol) was added over 12 minutes. After stirring for 10 minutes at 0° C., the reaction was warmed to room temperature. The reaction was quenched with $CH_3OH$ after 2 hours at room temperature. The THF was removed from the reaction mixture to give a slurry which was triturated with petroleum ether, and subsequently, filtered through a Celite pad in a sintered glass funnel. The solids were then boiled in petroleum ether and refiltered as above. The resulting yellow oil was passed through 50 g of Florisil (100–200 mesh) eluted with ~400 mL of petroleum ether providing the title tetraene (3.36 g, 86%) as a clear oil after solvent removal.

TLC Silica gel (20% ethyl acetate/hexane) $R_f=0.68$.

$^1$H NMR (CDCl$_3$, 270 MHz): 6.56 (ddd, 1H, J=17, 12, 6 Hz), 5.85 (d, 1H, J=12 Hz), 5.10 (m, 2H), 5.02 (m, 2H), 2.05 (m, 8H), 1.75 (s, 3H), 1.67 (s, 3H), 1.60 (s, 6H) ppm.

$^{13}$C-NMR (CDCl$_3$, 67.8 MHz): δ 139.3, 135.3, 133.4, 131.2, 125.5, 124.3, 123.9, 114.5, 39.9, 39.7, 26.8, 26.4, 25.6, 17.7, 16.6, 15.9 ppm.

(3) (E,E)-4,8,12-Trimethyl-3,7,11-tridecatrien-1-ol

Neat 2-methyl-2-butene (2.25 g, 0.032 mol) was added to a 1.0M BH$_3$-THF solution (16.9 mL) at −50° C. and under argon. After the addition was complete, the reaction was stirred for 2 hours at 0° C. The resulting disiamylborane solution was transferred via cannula over 1 hour to a flask containing a 17 mL THF solution of Part A(2) tetraene (3.36 g, 0.015 mol) under argon atmosphere and cooled to 0° C. After the transfer was complete, the reaction was allowed to gradually warm to room temperature, and then it was stirred overnight at room temperature. The reaction mixture was cooled to 0° C., and 5.1 mL of 3N NaOH was added rapidly. After stirring for 10 minutes, the reaction mixture was cooled in an ice-salt bath and 5.1 mL of 30% H$_2$O$_2$ was added dropwise. Subsequently, the reaction was warmed to room temperature and stirred for 4 hours after which it was diluted with H$_2$O, and the resulting aqueous layer was extracted several times with ethyl ether. The combined organic layers were dried over MgSO$_4$. Purification by flash chromatography eluting with 20% ethyl acetate/hexane provided the title alcohol (2.62 g, 74%) as a clear oil.

TLC Silica gel (20% ethyl acetate/hexane) $R_f=0.23$.

IR (Film) 3340 (br), 2965, 2920, 1665, 1440, 1380, 1100, 1050 cm$^{-1}$.

$^1$H NMR (CDCl$_3$, 270 MHz): δ 5.10 (m, 3H), 3.61 (t, 2H, J=6 Hz), 2.29 (q, 2H, J=6 Hz), 2.03 (m, 8H), 1.67 (s, 3H), 1.65 (s, 3H), 1.60 (s, 6H) ppm.

$^{13}$C NMR (CDCl$_3$, 67.8 MHz): δ 138.8, 135.2, 131.2, 124.3, 123.9, 119.9, 62.4, 39.8, 39.7, 31.5, 26.7, 26.5, 25.6, 17.6, 16.1, 15.9 ppm.

B. (E,E)-4,8,12-Trimethyl-3,7,11-tridecatriene-1-ol, methanesulfonate ester

To a stirred solution of 2.0 g (8.5 mmol) of Part A compound in 25 mL of CH$_2$Cl$_2$ at 0° C. under argon was added 1.5 mL (11.0 mmol) of triethylamine, a few crystals of 4-dimethylaminopyridine (catalyst), followed by 789 μL (10.2 mmol) of methanesulfonyl chloride dropwise. The mixture was stirred at 0° C. for 1 hour and then was diluted with 150 mL of ethyl ether. The organic layer was washed with KHSO$_4$, NaHCO$_3$, brine and dried over MgSO$_4$. The solvent was evaporated to provide 2.67 g (100%) of title compound as a yellow oil.

TLC: Silica gel (CH$_2$Cl$_2$) $R_f=0.49$.

$^1$H NMR (CDCl$_3$, 270 MHz): δ 5.10 (m, 3H), 3.59 (t, 2H, J=6.7 Hz), 2.30–1.70 (m, 11H), 1.67 (s, 3H), 1.64 (s, 3H), 1.60 (s, 6H) ppm.

C. (E,E)-4,8,12-Trimethyl-3,7,11-tridecatrien-1-yl iodide

To a stirred solution of 2.0 g (8.5 mmol) of Part B compound in 90 mL of acetone at room temperature under argon was added 2.55 g (17.0 mmol) of NaI. The mixture was refluxed at 80° C. for 4 hours, cooled to room temperature and diluted with 200 mL of 1:1 hexane:water. The organic layer was dried over MgSO$_4$ and evaporated under reduced pressure to provide 2.5 g of title compound as a pale yellow oil. Flash chromatography was performed on 30 g of silica gel (60–200 mesh), packed, loaded and eluted with hexane. The pure product fractions were combined and evaporated to provide 1.97 g (69%) of title compound as a pale oil.

TLC: Silica gel (Hexane) $R_f=0.35$.

IR (CCl$_4$) 2964, 2922, 2852, 1662, 1442, 1381, 1354, 1329, 1292, 1244, 1207, 1165, 1107, 983, 916, 887, 837, 815, 796, 742 cm$^{-1}$.

$^1$H NMR (270 MHz, CDCl$_3$): δ 5.10 (m, 3H), 3.10 (t, 2H, J=6.5 Hz), 2.55 (q, 2H, J=7.3 Hz), 2.10–1.00 (m, 8H), 1.68 (s, 3H), 1.61 (s, 3H), 1.60 (s, 6H) ppm.

Mass Spec (CI-NH$_3$ + ions) m/e 364 (M+NH$_4$), 347 (M+H).

D. (E,E)-2-(Diethoxyphosphinyl)-6,10,14-trimethyl-5,9,13-pentadecatrienoic acid, 1,1-dimethylethyl ester To a stirred solution of 209 mg (8.70 mmol) of NaH in 15 mL of THF at 0° C. under argon was added dropwise 2.19 g (8.70 mmol) of t-butyldiethyl phosphonoacetate. The mixture stirred for 0.5 h at 0° C. at which time 1.0 g (2.90 mmol) of Part C iodide was added dropwise. The mixture was warmed to RT over 2 h and stirred for 18 h, then was diluted with ether and quenched with NH$_4$Cl. The organic layer was washed with water, brine, dried over MgSO$_4$ and the solvent evaporated to provide 2.0 g of a colorless oil. Flash chromatography was performed on 50 g of silica gel eluted with 60:40 hexane/EtOAc. The pure product fractions were combined and evaporated to provide 920 mg (68%) of title compound as a colorless oil.

TLC Silica gel (1:1 hexane/EtOAc) $R_f=0.45$.

IR 2980, 2930, 2856, 1728, 1442, 1392, 1367, 1334, 1290, 1253, 1163, 1141, 1097, 1055, 1028, 966, 792, cm$^{-1}$.

$^1$H NMR (270 MHz, CDCl$_3$) δ 5.10 (m, 3H) 4.10 (m, 4H) 2.80 (ddd,1H, J=3.5, 10.3, 22.3 Hz) 2.00 (m, 10H) 1.80 (m, 2H) 1.67 (s, 3H) 1.60 (s, 9H) 1.50 (s, 9H) 1.30 (t, 6H, J=7.04 Hz) ppm.

Mass Spec (CI-NH$_3$, + ions) m/e 488(M+NH$_4$), 471 (M+H).

E. (E,E)-6,10,14-Trimethyl-2-phosphono-5,9,13-pentadecatrienoic acid, trisodium salt To a stirred solution of 920 mg (1.96 mmol) of Part D compound in 10 mL CH$_2$Cl$_2$ at 0° C. under argon was added 777 μL (5.88 mmol) of 2,4,6-collidine and 1.26 mL (8.82 mmol) of iodotrimethylsilane. The mixture stirred at 0° C. for 10 min. and was heated to 40° for 18 h at which point the solvent was evaporated and pumped at high vacuum for 20 min. The remainder was dissolved in 28.2 mL (14.10 mmol) of 0.5M NaOH and lyophilized. The crude material was purified by MPLC on a column of CHP20P gel (2.5 cm diameter×13.5 height), eluted with water (fractions 1 to 15) followed by a gradient created by the gradual addition of 400 mL of 75:25 CH₃CN/H₂O to a reservoir of 400 mL of H₂O. Approximately 15 mL fractions collected. Pure product fractions were combined and evaporated to a 100 mL volume, then lyophilized to provide 570 mg (69%) of title salt as a white lyophilate.

TLC Silica gel (4:4:1 n-propanol/conc. NH$_3$/H$_2$O) R$_f$=0.50.

IR 3435, 3051, 2966, 2924, 2856, 1635, 1568, 1446, 1388, 1159, 1084, 974, 900, 850 cm$^{-1}$.

$^1$H NMR (400 MHZ, D$_2$O) δ 5.20 (t, 1H, J=6.96 Hz) 5.15, 5.10 (two t, 2H, J=6.96 Hz) 2.45 (ddd, 1H, J=2.9, 11.7, 20.9 Hz) 2.10–1.70 (m, 11 H) 1.67–1.50 (m, 2H) 1.62 (s, 3H) 1.56 (s, 9H) ppm.

Mass Spec (FAB, + ions) m/e 447 (M+Na), 425 (M+H), 403 (M-Na+2H), 381 (M-2Na+3H).

Anal. calc'd for C$_{18}$H$_{28}$O$_5$PNa$_3$+0.70 H$_2$O: C, 49.47 H, 6.78 P, 7.09. Found C, 49.28 H, 7.00 P, 7.44.

EXAMPLE 13

(E)-7,11-Dimethyl-2-phosphono-6,10-dodecadienoic acid, disodium salt

A. (E)-8-Chloro-2,6-dimethyl-2,6-octadiene

To a stirred solution of 30.0 g (0.194 mol) of (E)-3,7-dimethyl-2,6-octadien-1-ol and 28.27 mL (0.213 mol) of 2,4,6-collidine under argon at room temperature was added dropwise 8.23 g (0.194 mol) of lithium chloride in 100 mL of DMF. The mixture was cooled at 0° C. and treated with 16.56 mL (0.213 mmol) of methanesulfonyl chloride dropwise over 10 minutes. The reaction was stirred at 0° C. for 1.5 hours (solid present), then was poured into 500 mL of ice/water. The aqueous solution was washed three times with 200 mL portions of hexane, the organic layers were combined and washed with 5% KHSO$_4$, water, NaHCO$_3$, brine, dried (MgSO$_4$) and evaporated to provide 29.95 g of a pale yellow oil. Rapid flash chromatography was performed on 400 g of silica gel, eluting with 3:9 EtOAc/hexane. Pure product fractions were combined and evaporated to provide 25.20 g (75%) of title compound as a pale yellow oil.

TLC Silica gel (8:1 hexane/EtOAc) R$_f$=0.68.

$^1$H-NMR (CDCl$_3$, 270 MHz): δ 5.44 (m, 1H), 5.08 (m, 1H), 4.09 (d, 2H, J=8.2 Hz), 2.08 (m, 4H), 1.73 (s, 3H), 1.68 (s, 3H), 1.60 (s, 3H) ppm.

B. (E)-(3,7-Dimethyl-2,6-octadienyl)propanedioic acid, diethyl ester

To a stirred solution of 14.68 g (0.611 mol) of NaH (100%) in 400 mL of THF at 0° C. under argon was added dropwise 92.76 mL (0.611 mol) of diethyl malonate in 100 mL of THF over 0.5 hours. This solution was stirred for 0.5 hours at 0° C., at which time 35.20 g (0.204 mol) of Part A chloride in 50 mL of THF was added dropwise over 15 minutes. The reaction gradually warmed to room temperature, stirred for 18 hours then was quenched with 250 mL of saturated NH$_4$Cl and diluted with 250 mL of ether. The organic layer was washed with water, brine, dried (MgSO$_4$) and evaporated to remove solvent and provide 100 g of an oil. The excess diethyl malonate was removed by distillation at 75° C. (1.5 mm) to provide 65 g of title compound also containing some dialkylated product and diethyl malonate.

TLC Silica gel (1:1 hexane/ethyl acetate) R$_f$=0.37.

IR (CCl$_4$) 2982, 2926, 2854, 1751, 1734, 1446, 1369, 1332, 1269, 1236, 1209, 1149, 1111, 1095, 1035, 860 cm$^{-1}$.

$^1$H NMR (CDCl$_3$, 270 MHz): δ 5.07 (q, 2H, J=7.1 Hz), 4.18 (q, 2H, J=7.0 Hz), 3.33 (t, 1H, J=7.6 Hz), 2.60 (t, 2H, J=7.3 Hz), 2.04–1.98 (m, 9H), 1.68 (s, 3H), 1.64 (s, 3H), 1.59 (s, 3H), 1.26 (t, 6H, J=7.0 Hz) ppm.

Mass Spec (CI-NH$_3$, + ions) m/e 314 (M+NH$_4$), 297 (M+H).

C. (E)-5,9-Dimethyl-4,8-decadienoic acid, ethyl ester

To a solution of 65 g of the crude Part B diester described above, 5.40 mL (0.30 mol) of water and 25.0 g (0.60 mol) of lithium chloride in 250 mL of DMSO was heated to 190° C. and stirred for 9 hours. The reaction was treated with a 1:1 solution of hexane/ether and then washed with water and brine. The organic layer was dried (MgSO$_4$) and evaporated to provide 34.6 g of title compound in the form of a yellow oil. No further purification was performed; the sample was carried on to the next step.

TLC Silica gel (95:5 hexane/ethyl acetate) R$_f$=0.30.

$^1$H NMR (CDCl$_3$, 270 MHz): δ 5.00 (m, 2H), 4.04 (q, 2H, J=7.0 Hz), 2.23 (m, 4H), 1.99–1.87 (m, 4H), 1.59 (s, 3H), 1.54 (s, 3H), 1.51 (s, 3H), 1.17 (t, 3H, J=7.0 Hz) ppm.

Mass Spec (CI-NH$_3$, + ions) m/e 242 (M+NH$_4$), 225 (M+H).

D. (E)-5,9-Dimethyl-4,8-decadien-1-ol

To a stirred solution of 5.84 g (0.154 mol) of lithium aluminum hydride in 700 mL of ether at 0° C. under argon was added dropwise 34.50 g of crude Part C ester over 20 minutes. The mixture was stirred for 1.5 hours at which time it was quenched by the following: 5.8 mL (0.324 mol) of water, 5.8 mL of 5% NaOH in water and then 17.5 mL (0.973 mol) of water. The granular solution was stirred and dried (MgSO$_4$) for 0.5 hours at which time the mixture was filtered through a celite cake and washed with ether followed by dichloromethane. The filtrate was evaporated to provide 28.16 g of an oil that was distilled using a short-path apparatus (bp 95°–96° C., 0.3 mm) to provide 20.5 g (55% overall from Part A chloride) of title alcohol as a colorless oil.

TLC Silica gel (Dichloromethane) R$_f$=0.11.

IR (CCl$_4$) 3620, 3340, 2966, 2924, 2877, 2856, 2729, 1670, 1446, 1377, 1350, 1278, 1199, 1155, 1107, 1057, 985, 829, 814, 792 cm$^{-1}$.

$^1$H NMR (CDCl$_3$, 270 MHz): δ 5.10 (m, 2H), 3.62 (t, 2H, J=6.5 Hz), 2.11–1.94 (m, 7H), 1.67–1.58 (m, 2H), 1.67 (s, 3H), 1.61 (s, 3H) ppm.

Mass Spec (CI-NH$_3$, + ions) m/e 200 (M+NH$_4$), 183 (M+H).

E. (E)-5,9-Dimethyl-4,8-decadien-1-ol, methanesulfonate ester

To a stirred solution of 12.0 g (65.93 mmol) of Part D alcohol in 200 mL of dichloromethane at 0° C. under argon was added 11.95 mL (85.71 mmol) of triethylamine and 6.12 mL (79.12 mmol) of methanesulfonyl chloride. The reaction was stirred for 1 hour then was diluted with ether and washed with 5% KHSO$_4$, saturated NaHCO$_3$ and brine. The organic layer was dried (MgSO$_4$) and evaporated to provide 16.91 g (98%) of title methanesulfonate as a pale yellow oil.

TLC Silica gel (Dichloromethane) R$_f$=0.53.

IR (CCl$_4$) 2963, 2927, 2922, 2882, 2875, 2856, 1455, 1450, 1381, 1363, 1347, 1178, 1007, 969, 957, 929, 793, 785, 758 cm$^{-1}$.

$^1$H NMR (CDCl$_3$, 270 MHz): δ 5.09 (m, 2H), 4.21 (t, 2H, J=6.5 Hz), 2.98 (s, 3H), 2.13–1.99 (m, 6H), 1.79

(quint., 2H, J=6.7 Hz), 1.68 (s, 3H), 1.61 (s, 3H), 1.60 (s, 3H) ppm.

Mass Spec (CI-NH$_3$, + ions) m/e 278 (M+NH$_4$).

F. (E)-(E)-5,9-Dimethyl-4,8-decadien-1-yl iodide

To a stirred solution of 16.91 g (65.04 mmol) of Part E methanesulfonate in 500 mL of acetone at room temperture under argon was added 39.00 g (260.16 mmol) of sodium iodide. The reaction mixture was refluxed for 3.5 hours, then diluted with 400 mL of a 1:1 mixture of water/hexane. The organic layer was washed with saturated sodium sulfite, dried (MgSO$_4$) and evaporated to provide 17.57 g of a pale yellow oil. The oil residue was filtered through 400 g of silica gel eluting with hexane. The pure product fractions were combined and evaporated to provide 16.86 g (89%) of title iodide as a colorless oil.

TLC Silica gel (Hexane) R$_f$=0.37.

IR (CCl$_4$) 2962, 2924, 2852, 1444, 1375, 1342, 1261, 1226, 1201, 1163, 1107, 983, 873, 835, 819, 761, 742 cm$^{-1}$.

$^1$H NMR (CDCl$_3$, 270 MHz): δ 5.07 (t, 2H, J=7.0 Hz), 3.18 (t, 2H, J=7.0 Hz), 3.14–1.96 (m, 6H), 1.86 (quint., 2H, J=7.0 Hz), 1.68 (s, 3H), 1.63 (s, 3H), 1.60 (s, 3H) ppm.

G. (E)-2-(Diethoxyphosphinyl)-7,11-dimethyl-6,10-dodecatrienoic acid, 1,1-dimethylethyl ester To a stirred solution of 247 mg (10.27 mmol) of NaH in 14 mL of DMF at 0° C. under argon was added dropwise 2.59 g (10.27 mmol) of t-butyldiethyl phosphonoacetate in 2 mL of DMF. The mixture was stirred for 0.5 h at 0° C., at which time 1.0 g (3.42 mmol) of Part F iodide was added dropwise. The reaction was stirred at 0° C. for 1 h, RT for 18 h, then was diluted with ether and quenched with sat. NH$_4$Cl. The organic layer was washed with water, brine, dried (MgSO$_4$) and evaporated to provide 2.20 g of a pale yellow oil. Flash chromatography was performed on 200 g of silica gel, eluting with 3:97 methanol/dichloromethane. Product fractions were combined and evaporated to provide 1.64 g of a colorless oil which required further purification. The volatile impurities were distilled off (130° C., ~1.0 mm) to leave 1.11 g (79%) of title compound as a colorless oil.

TLC gel (5:95 methanol/dichloromethane) R$_f$=0.70.

IR (CCl$_4$) 2981, 2931, 1730, 1454, 1368, 1255, 1156 cm$^{-1}$.

$^1$H NMR (270 MHz, CDCl$_3$) δ 5.10 (m, 2H) 4.25 (m, 4H) 2.83 (ddd, 1H, J=3.8, 10.9, 22.9 Hz) 2.00 (m, 6H) 1.83 (m, 2H) 1.68 (s, 3H) 1.59 (s, 6H) 1.48 (s, 9H) 1.40 (m, 2H) 1.33, 1.32 (two t, 6H, J=7.0 Hz) ppm.

Mass Spec (CI-NH$_3$, + ions) m/e 434 (M+NH$_4$), 417 (M+H).

H. (E)-7,11-Dimethyl-2-phosphono-6,10-dodecadienoic acid, disodium salt

To a stirred solution of 1.10 g (2.64 mmol) of Part G compound in 10 mL of CH$_2$Cl$_2$ at RT under argon was added 698 μL (5.28 mmol) of 2,4,6-collidine followed by 1.50 mL (10.56 mmol) of iodotrimethylsilane. The reaction was heated to 40° C. for 24 h, the solvent was evaporated and the residue was pumped on at high vacuum for 2 h. The remainder was treated with 8.70 mL (8.70 mmol) of 1M NaOH and lyophilized. The crude lyophilate was precipitated by dissolving the sample in 5.0 mL of water, warming to 50° C., treating the solution with 1.0 mL of acetone and placing the mixture in an ice bath for 0.5 h. The precipitate was filtered and treated with 10 mL of 5:1 water/acetone. This procedure was performed two times. The solid had a final wash with 20 mL of acetone and the fine solid was pumped on by high vacuum for 24 h to provide 665 mg (70%) of title salt as a cream colored solid.

TLC Silica gel (n-propanol/conc. NH$_3$/H$_2$O 5:4:1) R$_f$=0.37.

IR (KBr) 3434, 2927, 2858, 1577, 1443, 1384, 1175, 1074 cm$^{-1}$.

$^1$H NMR (400 MHz, D$_2$O) δ 5.20 (t, 1H, J=6.8 Hz) 5.12 (t, 1H, J=6.8 Hz) 2.54 (ddd, 1H, J=3.6, 11.5, 20.7 Hz) 2.10, 2.02 (two m, 6H) 1.80 (m, 2H) 1.63 (s, 3H) 1.56 (s, 6H) 1.35 (m, 2H) ppm.

Mass Spec (FAB, + ions) m/e 393 (M+2Na-H), 371 (M+Na), 349 (M+H), 327 (M+2H-Na).

Anal. calc'd for C$_{14}$H$_{23}$PO$_5$Na$_2$+0.45 mol H$_2$O: C, 47.19 ; H, 6.76 ; P, 8.69. Found: C, 47.19 ; H, 6.85 ; P, 8.91

EXAMPLE 14

α-Phosphono[1,1'-biphenyl]-4-pentanoic acid, tripotassium salt

A. 4-(3-Iodopropyl)[1,1'-biphenyl]

A(1) (E)-3-([1,1'-Biphenyl]-4-yl)-2-propenoic acid, methyl ester

Sodium hydride (2.40 g, 60 wt. % in mineral oil, 60.3 mmol) was washed with hexane (2×50 mL), then suspended in THF (125 mL) under argon. Trimethyl phosphonoacetate (9.8 mL, 60.3 mmol) was added to the suspension over 20 minutes (mild exotherm). A thick precipitate formed and was stirred at room temperature for 30 minutes, then at 50° C. for 30 minutes. After cooling to 0° C., a solution of [1,1-biphenyl]-4-carboxaldehyde (10.0 g, 54.9 mmol) in THF (40 mL) was added over 20 minutes, at which time the precipitate dissolved. The reaction mixture was allowed to stir at 0° C. for 1 hour, then at room temperature for 1 hour. The reaction mixture was diluted with CH$_2$Cl$_2$ and washed with saturated NH$_4$Cl and water, then dried over MgSO$_4$. Evaporation gave the crude product, which was recrystallized from EtOAc/hexane to afford title ester (7.82 g, 60%) as white plates (mp 147°–149° C.). The mother liquor was concentrated in vacuo and the resultant solid was recrystallized from MeOH to afford additional title compound (1.90 g, 15%) as white plates (mp 147°–149° C.). Total yield of title ester 9.72 g (75%).

TLC Silica gel (1:1 CH$_2$Cl$_2$/hexane) R$_f$=0.24.

IR (KBr) 3063, 2992, 2944, 1719, 1636, 1327, 1312, 1198, 1184, 1173, 984, 833, 772, 737, 689 cm$^{-1}$.

$^1$H NMR (CDCl$_3$, 270 MHz): δ 7.74 (d, 1H, J=16.4 Hz) 7.61 (m, 6H) 7.46 (t, 2H, J=7.6 Hz) 7.37 (m, 1H) 6.48 (d, 1H, J=16.4 Hz) 3.82 (d, 3H, J=1.2 Hz) ppm.

Anal. calc'd for C$_{16}$H$_{14}$O$_2$: C, 80.65; H, 5.92. Found: C, 80.38; H, 5.90.

A(2). [1,1'-Biphenyl]-4-propanoic acid, methyl ester

A mixture of Part A(1) ester (3.0 g, 12.6 mmol) and 10% palladium on carbon (150 mg) in THF (50 mL) was maintained under a balloon of hydrogen for 22 hours, then filtered through a layered pad of silica gel under Celite. The solids were washed with THF (200 mL), and the filtrate was evaporated to provide title ester (3.0 g, 99%) as a white solid. mp 58°–58.5° C.

TLC Silica gel (1:1 CH$_2$Cl$_2$/hexane) R$_f$=0.25.

IR (MeOH) 3485, 3432, 2951, 2838, 1742, 1657, 1449, 1411, 1166, 1026, 835, 754, 695 cm$^{-1}$.

$^1$H NMR (CDCl$_3$, 270 MHz): δ 7.57 (dm, 2H, J=7 Hz) 7.52 (dm, 2H, J=7 Hz) 7.42 (tm, 2H, J=7 Hz) 7.29 (m, 3H) 3.68 (s, 3H) 2.99 (t, 2H, J=7.6 Hz) 2.67 (t, 2H, J=7.6 Hz) ppm.

Anal. Calc'd for C$_{16}$H$_{16}$O$_2$: C, 79.97; H, 6.71. Found: C, 79.79; H, 6.67.

A(3). 4-(3-Iodopropyl)[1,1'-biphenyl]

Lithium aluminum hydride (17.6 mL, 1.0M in THF, 17.6 mmol) was added dropwise quickly over 15 minutes to a solution of Part A(2) ester (4.23 g, 17.6 mmol) in THF (100 mL) at 0° C. under argon. The opaque reaction mixture was stirred at 0° C. for an additional 15 minutes, then quenched by addition of hydrated Na$_2$SO$_4$ until gas evolution ceased. The resultant gelatinous suspension was diluted with EtOAc (100 mL), filtered through Celite, and washed with EtOAc (200 mL). The filtrate was evaporated to give 3.80 g of a white solid.

The alcohol prepared above was dissolved in CH$_2$Cl$_2$ and cooled to 0° C. under argon. Triethylamine (4.9 mL, 35.2 mmol) was added, followed by dropwise addition of methanesulfonyl chloride (1.5 mL, 19.4 mmol) over 5 minutes. The resultant cloudy yellow reaction mixture was stirred at 0° C. for 15 minutes, diluted with CH$_2$Cl$_2$ (200 mL), and washed with 1N HCl (75 mL), saturated NaHCO$_3$ (50 mL), and brine. After drying over MgSO$_4$, the solvent was evaporated to give 5.27 g of a white solid.

The mesylate prepared above was dissolved in acetone (150 mL) under argon. Sodium iodide (13.2 g, 88.0 mmol) was added, and the resultant heterogeneous mixture was heated to and maintained at reflux for 1.5 hours, then cooled to room temperature. The reaction mixture was concentrated in vacuo and the resultant yellow solid was partitioned between CH$_2$Cl$_2$ (150 mL) and water (75 mL). The organic layer was washed with brine (50 mL), then dried over MgSO$_4$. Evaporation gave a yellow oil, which was purified by flash chromatography on silica gel (75 g) eluting with hexane to give title iodide (5.27 g, 93%) as a colorless oil which crystallized on standing. mp 42°-44° C.

TLC Silica gel (Hexane) R$_f$=0.10.

IR (KBr) 3055, 3030, 2936, 1487, 1449, 1406, 1169, 752 cm$^{-1}$.

$^1$H NMR (CDCl$_3$, 270 MHz): δ 7.50, 7.55 (two dm, 2H each, J=7 Hz) 7.41 (tm, 2H, J=7 Hz) 7.31 (tm, 1H, J=7 Hz) 7.25 (d, 2H, J=7.6 Hz) 3.18 (t, 2H, J=7 Hz) 2.75 (t, 2H, J=7 Hz) 2.14 (quint, 2H, J=7 Hz) ppm.

Mass Spec (CI-NH$_3$, + ions) m/z 340 (M+NH$_4$), 322 (M+H).

Anal. Calc'd for C$_{15}$H$_{15}$I: C, 55.92; H, 4.69. Found: C, 55.88; H, 4.57.

B. α-(Diethoxyphosphinyl) [1,1'-biphenyl]-4-pentanoic acid, ethyl ester

To a stirred suspension of sodium hydride (0.85 g, 35.19 mmol) in THF at 0° C. (ice bath) under argon, triethylphosphonoacetate (7.0 mL, 35.19 mmol) was added dropwise over 15 minutes. The ice bath was removed and the reaction mixture was stirred at room temperature until the solution was clear. The reaction mixture was recooled to 0° C. and a solution of Part A compound (3.8 g, 11.73 mmol) in THF (15 mL) was added dropwise over 15 minutes, and stirring was continued at 0° C. for 2 hours. The ice bath was removed and the reaction mixture was stirred at room temperature overnight. The reaction solution was diluted with ethyl ether (200 mL) and quenched with saturated NH$_4$Cl (100 mL). the organic layer was washed with water (100 mL) and brine (100 mL) then dried over MgSO$_4$. Evaporation gave a crude oil. Flash chromatography was performed on 300 g silica gel, loaded and eluted with ethyl acetate:hexane (45:55). The pure fractions (45-61) were combined and evaporated to provide 3.0 g (61%) of title compound as a colorless oil.

C. α-Phosphono[1,1'-biphenyl]-4-pentanoic acid, tripotassium salt

To a stirred solution of Part B compound (800 mg, 2.87 mmol) in 95% ethanol at room temperature under argon, was added 1M sodium hydroxide (2.87 mL). The mixture was heated to 55° C. and stirred for 24 hours, then cooled at room temperature, acidified with 1M KHSO$_4$ solution to pH 4 and extracted with ethyl acetate. The organic layer was dried over MgSO$_4$. Evaporation gave 750 mg of a colorless oil. The product was dissolved in dichloromethane (10 mL). To this solution, bis(trimethylsilyl)trifluoroacetamide (492 mg, 1.91 mmol) was added followed by bromotrimethylsilane (1.0 mL, 7.64 mmol). The mixture was stirred at room temperature for 20 hours. The solvent was evaporated and the residue was pumped at high vacuum for 2 hours. The residue was dissolved in 1M potassium hydroxide (8 mL) and lyophilized to give a white powder. The crude product was purified by chromatography on SP 207 gel (2.5×20 cm), loaded and eluted with water (1-14) and followed by gradual addition of CH$_3$CN to a reservoir of water. The combined pure fractions (17-44) were evaporated to remove CH$_3$CN and the remaining aqueous solution was lyophilized to provide 737 mg (86%) of title salt as a white solid.

IR (KBr) 2936, 1653, 1559, 1487, 1385, 1063, 970 cm$^{-1}$.

$^1$H NMR (D$_2$O, 400 MHz) δ 7.56 (d, 2H, J=7.7 Hz) 7.50 (d, 2H, J=7.3 Hz) 7.38 (t, 2H, J=17.5 Hz) 7.28 (m, 3H) 2.57 (m, 2H) 2.42 (m, 1H) 1.81-1-69 (m, 1H) 1.65-1.37 (m, 3H) ppm.

$^{13}$C NMR (D$_2$O, 100 MHz): δ 182,99 143.24 140.61 138.01 129.38 129.25 127.57 127.01 126.89 52.44 (d, J=116 Hz) 34.92 31.26 (d, J=15 Hz) 29.15 ppm.

Mass Spec (FAB, + ions) m/z 373 (M+3H-2K), 411 (M+2H-K), 449 (M+H), 487 (M+K).

Anal. Calc'd for C$_{17}$H$_{16}$K$_3$O$_5$P+2.5 equiv H$_2$O: C, 41.36; H, 4.29; P, 6.27. Found: C, 41.38; H, 4.15; P, 5.94.

Following the procedures set out hereinbefore the following additional compounds may be prepared:

8-([1,1'-biphenyl]-4-yl)-2-phosphonooctanoic acid, dipotassium salt;

Mass Spec (FAB) m/z 529 (M+2K-H), 491 (M+K), 453 (M+H).

Anal Calc'd for C$_{20}$H$_{23}$O$_5$PK$_2$+3.7 H$_2$O: C, 46.26; H, 5.90; P, 5.97. Found: C, 46.27; H, 5.59; P, 6.04.

α-phosphono-4'-propyl[1,1'-biphenyl]-4-pentanoic acid, tripotassium salt;

Mass Spec (FAB) m/z 529 (M+K), 491 (M+H).

Anal. Calc'd for C$_{20}$H$_{22}$O$_5$PK$_5$+2.0 H$_2$O: C, 45.61; H, 4.98; P, 6.31. Found: C, 45.43; H, 4.81; P, 6.08.

What is claimed is:

1. A compound having the structure

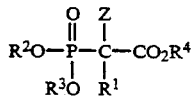

wherein
- $R^2$ and $R^3$ are independently H, a metal ion, other pharmaceutically acceptable cation, or a prodrug ester;
- $R^4$ is H, alkyl, aryl, alkenyl, arylalkyl, metal ion, other pharmaceutically acceptable cation, or a prodrug ester;
- $R^1$ is lipophilic group containing at least 7 carbons and is optionally substituted cycloalkyl, optionally substituted alkenyl containing 3 or 4 double bonds, optionally substituted alkynyl, or optionally substituted aryl; and
- Z is H, halogen, lower alkyl, hydroxy or hydroxyalkyl; including pharmaceutically acceptable salts thereof.

2. The compounds as defined in claim 1 wherein $R^1$ is alkenyl.

3. The compound as defined in claim 1 wherein $R^1$ is

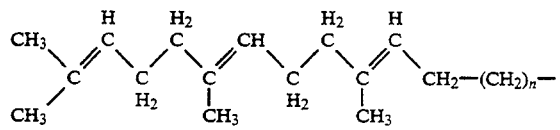

wherein n is 1, 2 or 3.

4. The compound as defined in claim 3 wherein Z is H, $CH_3$, Cl, F, OH or $CH_2OH$.

5. The compound as defined in claim 1 wherein Z is H, halogen, hydroxy or hydroxymethyl; $R^1$ is alkenyl; $R^2$ and $R^3$ are Na, K or H; and $R^4$ is H, Na or K.

6. The compound as defined in claim 4 wherein Z is H.

7. The compound as defined in claim 1 wherein $R^2$ and $R^3$ are Na, K or H, and $R^4$ is H, Na, K or alkyl, aryl or arylalkyl.

8. The compound as defined in claim 7 wherein $R^2$, $R^3$ and $R^4$ are Na or K.

9. The compound as defined in claim 7 wherein $R^2$ is Na or K, $R^3$ is H and $R^4$ is Na or K.

10. The compound as defined in claim 1, having the name (E,E)-6,10,14-trimethyl-2-phosphono-5,9,13-pentadecatrienoic acid, salts or esters thereof including the trisodium salt;

(E,E)-7,11,15-trimethyl-2-phosphono-6,10,14-hexadecatrienoic acid, salts or esters thereof including the trisodium salt;

(E,E)-2-dihydroxyphosphinyl)-8,12,16-trimethyl-7,11,15-heptadecatrienoic acid, salts or esters thereof including the trisodium salt;

(E,E)-2,7,11,15-tetramethyl-2-phosphono-6,10,14-hexadecatrienoic acid, salts or esters thereof including the disodium salt;

(E,E)-2-chloro-7,11,15-trimethyl-2-phosphono-6,10,14-hexadecatrienoic acid, salts or esters thereof including the trisodium salt;

(E,E)-2-fluoro-7,11,15-trimethyl-2-phosphono-6,10,14-hexadecatrienoic acid, salts or esters thereof including the trisodium salt;

(E,E)-2-hydroxy-7,11,15-trimethyl-2-phosphono-6,10,14-hexadecatrienoic acid, salts or esters thereof including the trisodium salt;

(E,E)-2-hydroxymethyl-7,11,15-trimethyl-2-phosphono-6,10,14-hexadecatrienoic acid, salts or esters thereof including the trisodium salt;

(E,E)-7,11,15-trimethyl-2-phosphono-6,10,14-hexadecatrienoic acid, salts or esters thereof including the 3-phenylpropyl ester, disodium salt;

(E,E)-7,11,15-trimethyl-2-phosphono-6,10,14-hexadecatrienoic acid, ethyl ester, salts or esters thereof including the disodium salt.

11. The compound as defined in claim 1 wherein one or more of $R^2$, $R^3$ and $R^4$ are an alkali metal salt or alkaline earth metal salt.

12. The compound as defined in claim 1 wherein $R^2$, $R^3$ and $R^4$ are each H.

13. The compound as defined in claim 2 where $R^4$ is lower alkyl, lower alkenyl or arylalkyl.

14. A hypocholesterolemic or hypolipemic composition comprising a compound as defined in claim 1 and a pharmaceutically acceptable carrier therefor.

15. A combination comprising a compound as defined in claim 1 and an antihyperlipoproteinemic agent.

16. The combination as defined in claim 15 wherein said antihyperlipoproteinemic agent is probucol, gemfibrozil, a bile acid sequestrant, clofibrate, nicotinic acid, neomycin, p-aminosalicylic acid, bezafibrate, or an HMG CoA reductase inhibitor.

17. The combination as defined in claim 16 the bile acid sequestrant is cholestyramine, colestipol or polidexide the HMG CoA reductase inhibitor is lovastatin, pravastatin or simvastatin.

* * * * *